(12) United States Patent
Beutner et al.

(10) Patent No.: US 9,242,917 B2
(45) Date of Patent: Jan. 26, 2016

(54) CRYSTAL FORMS OF A HCV PROTEASE INHIBITOR

(75) Inventors: Gregory L Beutner, Green Brook, NJ (US); Robert M Wenslow, Jr., Cream Ridge, NJ (US); Eric J Choi, Libertyville, IL (US); Clinton Scott Shultz, South Orange, NJ (US); Jeremy Scott, Hoddesdon (GB); Juan D Arredondo, West Orange, NJ (US); Laura Artino, Oakhurst, NJ (US)

(73) Assignees: Merck Sharp & Dohme Limited, Hertfordshire (GB); Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/239,389

(22) PCT Filed: Aug. 16, 2012

(86) PCT No.: PCT/US2012/051168
§ 371 (c)(1),
(2), (4) Date: Feb. 18, 2014

(87) PCT Pub. No.: WO2013/028465
PCT Pub. Date: Feb. 28, 2013

(65) Prior Publication Data
US 2014/0206605 A1    Jul. 24, 2014

Related U.S. Application Data

(60) Provisional application No. 61/539,540, filed on Sep. 27, 2011, provisional application No. 61/533,915, filed on Sep. 13, 2011, provisional application No. 61/533,439, filed on Sep. 12, 2011, provisional application No. 61/525,462, filed on Aug. 19, 2011.

(51) Int. Cl.
| | |
|---|---|
| *C07K 5/08* | (2006.01) |
| *C07C 35/04* | (2006.01) |
| *C07K 5/083* | (2006.01) |
| *C07D 403/12* | (2006.01) |
| *C07D 498/16* | (2006.01) |
| *C07K 5/12* | (2006.01) |
| *C07C 67/14* | (2006.01) |
| *C07C 69/013* | (2006.01) |
| *C07C 69/12* | (2006.01) |
| *C07C 269/04* | (2006.01) |
| *C07C 271/34* | (2006.01) |
| *A61K 38/00* | (2006.01) |

(52) U.S. Cl.
CPC ........... *C07C 35/04* (2013.01); *C07C 67/14* (2013.01); *C07C 69/013* (2013.01); *C07C 69/12* (2013.01); *C07C 269/04* (2013.01); *C07C 271/34* (2013.01); *C07D 403/12* (2013.01); *C07D 498/16* (2013.01); *C07K 5/0808* (2013.01); *C07K 5/126* (2013.01); *A61K 38/00* (2013.01)

(58) Field of Classification Search
CPC ............................................. C07K 5/00–5/126
See application file for complete search history.

(56) References Cited

U.S. PATENT DOCUMENTS

| | | | |
|---|---|---|---|
| 4,871,868 | A | 10/1989 | Saito et al. |
| 5,715,960 | A | 2/1998 | Seymour |
| 7,507,262 | B2 | 3/2009 | Lim et al. |
| 2003/0186939 | A1 | 10/2003 | Tani et al. |
| 2009/0155209 | A1 | 6/2009 | Blatt et al. |
| 2009/0216016 | A1 | 8/2009 | Yoshida et al. |
| 2009/0286778 | A1 | 11/2009 | Combs et al. |
| 2010/0029666 | A1 | 2/2010 | Harper et al. |
| 2014/0200343 | A1* | 7/2014 | Xu et al. .................. 540/457 |

FOREIGN PATENT DOCUMENTS

| | | |
|---|---|---|
| WO | WO2006102087 | 9/2006 |
| WO | WO2006119061 | 11/2006 |
| WO | WO2007015787 | 2/2007 |
| WO | WO2007015855 | 2/2007 |
| WO | WO2007016441 | 2/2007 |
| WO | WO2007131966 | 11/2007 |
| WO | WO2007148135 | 12/2007 |
| WO | WO2008051477 | 5/2008 |
| WO | WO2008051514 | 5/2008 |
| WO | WO2008057208 | 5/2008 |
| WO | WO2008057209 A1 | 5/2008 |
| WO | WO2009010804 | 1/2009 |
| WO | WO2009108507 | 9/2009 |
| WO | WO2009134624 | 11/2009 |
| WO | WO2010011566 | 1/2010 |
| WO | WO2011014487 | 2/2011 |
| WO | WO2013028465 | 2/2013 |
| WO | WO2013028470 | 2/2013 |
| WO | WO2013028471 | 2/2013 |

OTHER PUBLICATIONS

Bassan et al, Multikilogram-Scale Synthesis of a Chiral Cyclopropanol and an Investigation of the Safe Use of Lithium Acetylide-Ethylene Diamine Complex, Org. Process Res. Dev., 2012, 87-95, 16.

C. Balsano, Recent Advances in Antiviral Agents: Established and Innovative Therapies for Viral Hepatitis, Mni-Reviews in Medicinal Chemistry, 2008, pp. 307-318, 8(4).

De Francesco, Approaching a new era for hepatitis C virus therapy: inhibitors of the NS3-4A serine protease and the NS5B RNA-dependent RNA polymerase, Antiviral Research, 2003, 1-16, 58.

Gallinari et al, Modulation of Hepatitis C Virus NS3 Protease and Helicase Activities through the Interaction with NS4A, Biochemistry, 1999, 5620-5632, 38.

Gallinari et al, Multiple Enzymatic Activities Associated with Recombinant NS3 Protein of Hepatitis C Virus, J. Virol., 1998, 6758-6759, 72, No. 8.

Liverton et al, Mk-7009, a Potent and Selective Inhibitor of Hepatitis C Virus NS3/4A Protease, Antimicrobial Agents and Chemotherapy, 2010, 305-311, 54, No. 1.

Liverton et al, Molecular Modeling Based Approach to Potent P2-P4 Macrocyclic Inhibitors of Hepatitis C NS3/4A Protease, J. Am. Chem. Soc., 2008, 4607-4609, 130.

(Continued)

*Primary Examiner* — Christina Bradley
(74) *Attorney, Agent, or Firm* — Julie M. Lake; Laura M. Ginkel

(57) ABSTRACT

The present invention relates to different forms of a HCV inhibitory compound.

6 Claims, 15 Drawing Sheets

(56) References Cited

OTHER PUBLICATIONS

Mao, A time-resolved, internally quenched fluorescence assay to characterize inhibition of hepatitis C virus nonstructural protein 3-4A protease of low enzyme concentrations, Analytical Biochemistry, 2008, 1-8, 373.

Ronn, New Developments in the Discovery of Agents to Treat Hepatitis C, Current Topics in Medicinal Chemistry, 2008, 533-562, 8.

Sarges et al, 4-Amino[1,2,4]triazolo[4,3-a]quinoxalines. A Novel Class of Potent Adenosine Receptor Antagoists and Potential Rapid-Onset Antidepressants, J. Med. Chem., 1990, 2240-2254, 33.

Sheldon, Novel protease and polymerase inhibitors for the treatment of hepatitis C virus infection, Expert Opinion Investig. Drugs, 2007, 1171-1181, 16(8).

Shirakawa et al, Preparation of (E)-1-Alkenylboronic Acid Pinacol Esters via Transfer of Alkenyl Group from Boron to Boron, Synthesis, 2004, 1814-1820, 11.

Song et al, Synthesis of Vaniprevir (MK-7009): Lactamization to Prepare a 22-Membered Macrocycle, J. Org. Chem., 2011, 7804-7815, 76.

Steven S. Carroll, Inhibition of Hepatitis C Virus RNA Replication by 2'-Modified Nucleoside Analogs, NPL-Carroll-11979, 2003, pp. 11979-84, 278(14).

Taliani et al, A Continuous Assay of Hepatitis C Virus Protease Based on Resonance Energy Transfer Depsipeptide Substrates, Anal. Biochem., 1996, 60-67, 240.

* cited by examiner $\delta_{(Carbon-13)}$ [ppm]

CRYSTAL FORMS OF A HCV PROTEASE INHIBITOR

CROSS-REFERENCE TO RELATED APPLICATIONS

This application is a National Stage application of International Patent Application No. PCT/US2012/051168, filed Aug. 16, 2012, which claims the benefit of U.S. Provisional Patent Application No. 61/525,462, filed Aug. 19, 2011, U.S. Provisional Patent Application No. 61/533,439, filed Sep. 12, 2011, U.S. Provisional Patent Application No. 61/533,915, filed Sep. 13, 2011, and U.S. Provisional Patent Application No. 61/539,540, filed Sep. 27, 2011.

FIELD OF THE INVENTION

The present invention relates to different forms of a HCV inhibitory compound. HCV inhibitory compounds have therapeutic and research applications.

BACKGROUND OF THE INVENTION

Hepatitis C virus (HCV) infection is a major health problem. HCV infection leads to chronic liver disease, such as cirrhosis and hepatocellular carcinoma, in a substantial number of infected individuals. Several virally-encoded enzymes are putative targets for therapeutic intervention, including a metalloprotease (NS2-3), a serine protease (NS3), a helicase (NS3), and an RNA-dependent RNA polymerase (NS5B).

Potential treatments for HCV infection are discussed in different references including Balsano, *Mini Rev. Med. Chem.* 8(4):307-318, 2008, Rönn et al., *Current Topics in Medicinal Chemistry* 8:533-562, 2008, Sheldon et al., *Expert Opin. Investig. Drugs* 16(8):1171-1181, 2007, and De Francesco et al., *Antiviral Research* 58:1-16, 2003.

Examples of publications describing macrolactam compounds able to inhibit HCV protease activity include McCauley et al., WO2011014487; Harper et al., WO2010011566; Liverton et al., WO2009134624; McCauley et al., WO2009108507; Liverton et al., WO2009010804; Liverton et al., WO2008057209; Liverton et al., WO2008051477; Liverton et al., WO2008051514; Liverton et at, WO2008057208; Crescenzi et al., WO2007148135; Di Francesco et al., WO2007131966; Holloway et al., WO2007015855; Holloway et al., WO2007015787; Holloway et al., WO2007016441; Holloway et al., WO2006119061; Liverton et al., *J. Am. Chem. Soc.*, 130:4607-4609, 2008; and Liverton et al., *Antimicrobial Agents and Chemotherapy* 54:305-311, 2010.

SUMMARY OF THE INVENTION

The present invention includes different forms of Compound A, or a pharmaceutically salt thereof:

Compound A

Aspects of the present invention directed to crystalline Compound A include a pharmaceutical composition comprising a therapeutically effective amount of the compound and a pharmaceutically acceptable carrier; treating an HCV infected patient with the compound; use of the compound in medicine; the preparation of a medicament for use in treating HCV in a patient; and methods of making Hydrate III from Compound A using acetone and water.

Other embodiments, aspects and features of the present invention are either further described herein or will be apparent from the ensuing description, examples and appended claims.

DETAILED DESCRIPTION OF THE INVENTION

Macrolactam compounds able to inhibit HCV activity have different uses including inhibiting HCV activity in vivo, inhibiting HCV activity in vitro, and inhibiting HCV NS3 enzymatic activity. In vivo inhibition of HCV activity can be used for therapeutic applications. Inhibiting HCV activity in vitro has different applications including being used to obtain HCV resistant mutants, further characterizing the ability of a functional group to inhibit HCV replicon or enzymatic activity, and studying HCV replication or protease activity.

Compound A is described in Harper et al., WO2010011566. Harper et al., WO2010011566 includes data illustrating the ability of Compound A to inhibit HCV replicon activity and NS3/4A.

Compound A Forms

Six different Compound A hydrates were identified (Forms I, II, III, IV, V and VI). Hydrate III was the most stable hydrate form identified.

Figure 1:
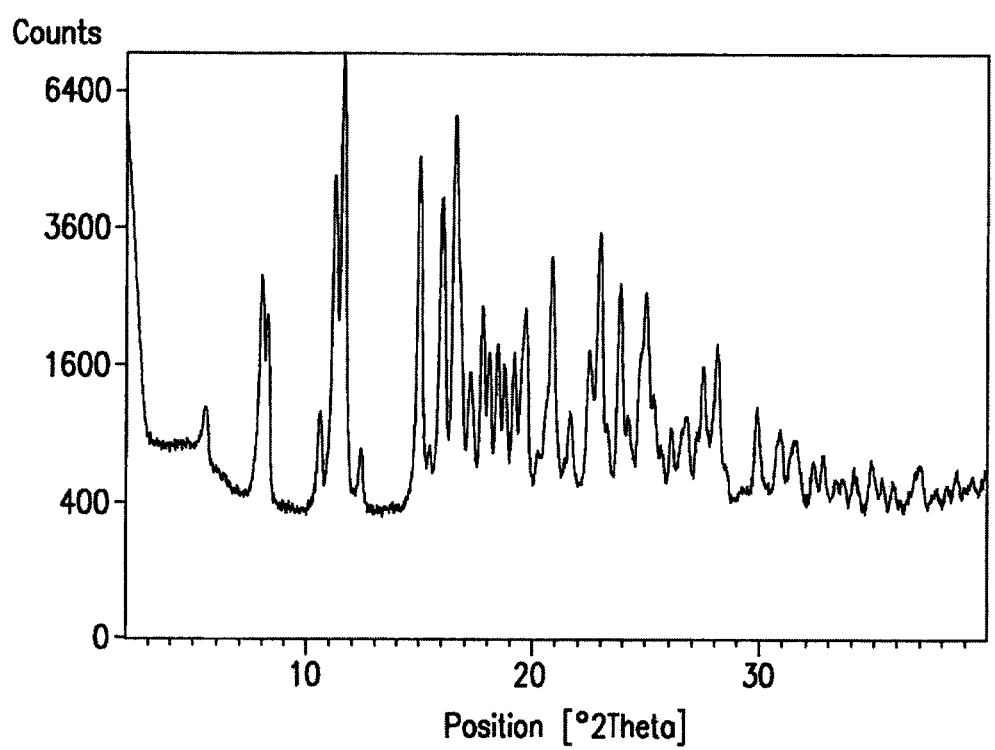
FIG. 1 illustrates an X-ray diffraction pattern of Compound A crystalline Hydrate II.

In a first embodiment directed to the Hydrate II, the hydrate is characterized by an X-ray powder diffraction pattern obtained using copper $K_\alpha$ radiation (i.e., the radiation source is a combination of Cu $K_{\alpha 1}$ and $K_{\alpha 2}$ radiation), which comprises three or more characteristic peaks. Characteristic peeks are illustrated in FIG. 1.

In a second embodiment, the hydrate is characterized by an X-ray powder diffraction pattern obtained using copper $K_\alpha$ radiation which comprises 2Θ values in degrees of about 2Θ values (i.e., reflections at 2Θ values) in degrees of about 11.7, 16.6, and 11.2

Reference to "about" with respect to 2Θ values provided herein indicates ±0.1.

In this embodiment and analogous embodiments which follow the term "about" is understood to modify each of the 2Θ values; e.g., the expression "about 11.7, 16.6, and 11.2" is short-hand for "about 11.7, about 16.6, and about 11.2".

In a third embodiment directed to the Hydrate II, the hydrate is characterized by an X-ray powder diffraction pattern obtained using copper $K_\alpha$ radiation which comprises 2Θ values in degrees of about 11.7, 16.6, 11.2, 15.1, and 16.1.

In a fourth embodiment directed to the Hydrate II, the hydrate is characterized by an X-ray powder diffraction pattern obtained using copper $K_\alpha$ radiation which comprises 2Θ values in degrees of about 11.7, 16.6, 11.2, 15.1, 16.1, 23.0, 20.9, 8.0, 23.9, 25.0, 16.8, 17.8, 19.8, 22.5, and 8.3.

In another embodiment, Hydrate II is substantially pure. Reference to "substantially pure" means the particular form makes up at least 50% of the compound present. In different embodiments, Hydrate II makes up at least 75%, at least 85%, at least 90%, at least 95%, or about 94%-98% of Compound A present.

Figure 2:
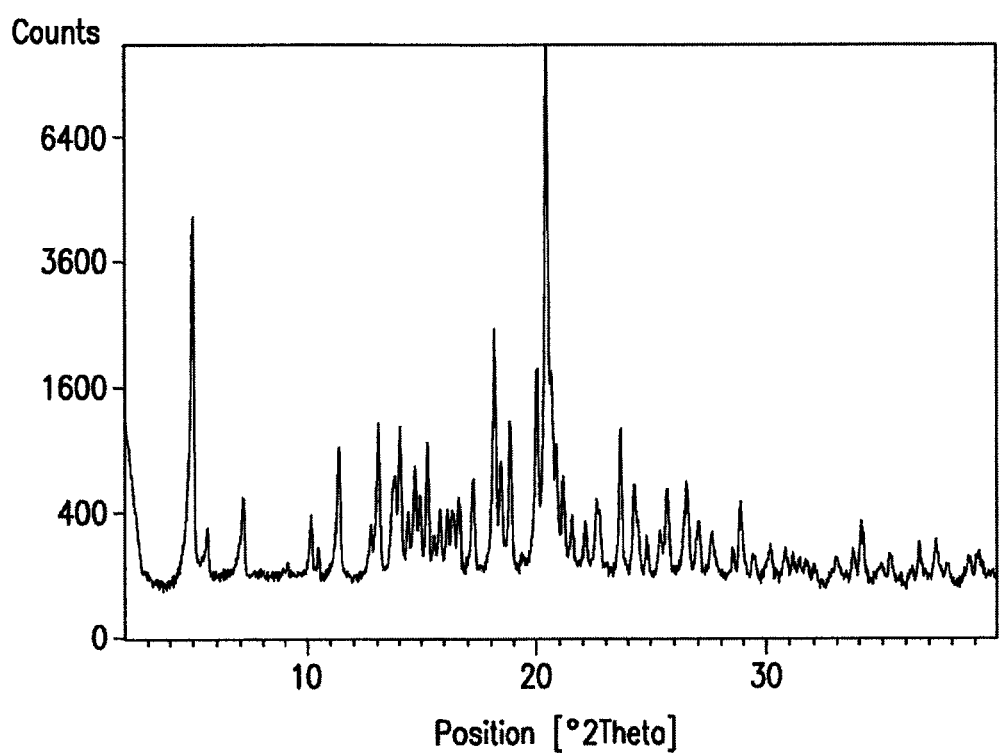
FIG. 2 illustrates an X-ray diffraction pattern of Compound A Hydrate III.

In a first embodiment directed to Hydrate III, the hydrate is characterized by an X-ray powder diffraction pattern obtained using copper $K_\alpha$ radiation which comprises three or more characteristic peaks. Characteristic peeks are illustrated in FIG. 2.

In a second embodiment directed to Hydrate III, the hydrate is characterized by an X-ray powder diffraction pattern obtained using copper $K_\alpha$ radiation which comprises 2Θ values in degrees of about 20.5, 5.0, and 18.2

In a third embodiment directed to Hydrate III, the hydrate is characterized by an X-ray powder diffraction pattern obtained using copper $K_\alpha$ radiation which comprises 2Θ values in degrees of about 20.5, 5.0, 18.2, 20.1, and 20.7.

In a fourth embodiment directed to Hydrate III, the hydrate is characterized by an X-ray powder diffraction pattern obtained using copper $K_\alpha$ radiation which comprises 2Θ values in degrees of about 20.5, 5.0, 18.2, 20.1, 20.7, 14.1, 23.7, 13.1, 18.9, 15.3, 20.9, 11.4, 18.4, 14.7, and 13.8.

Figure 3:
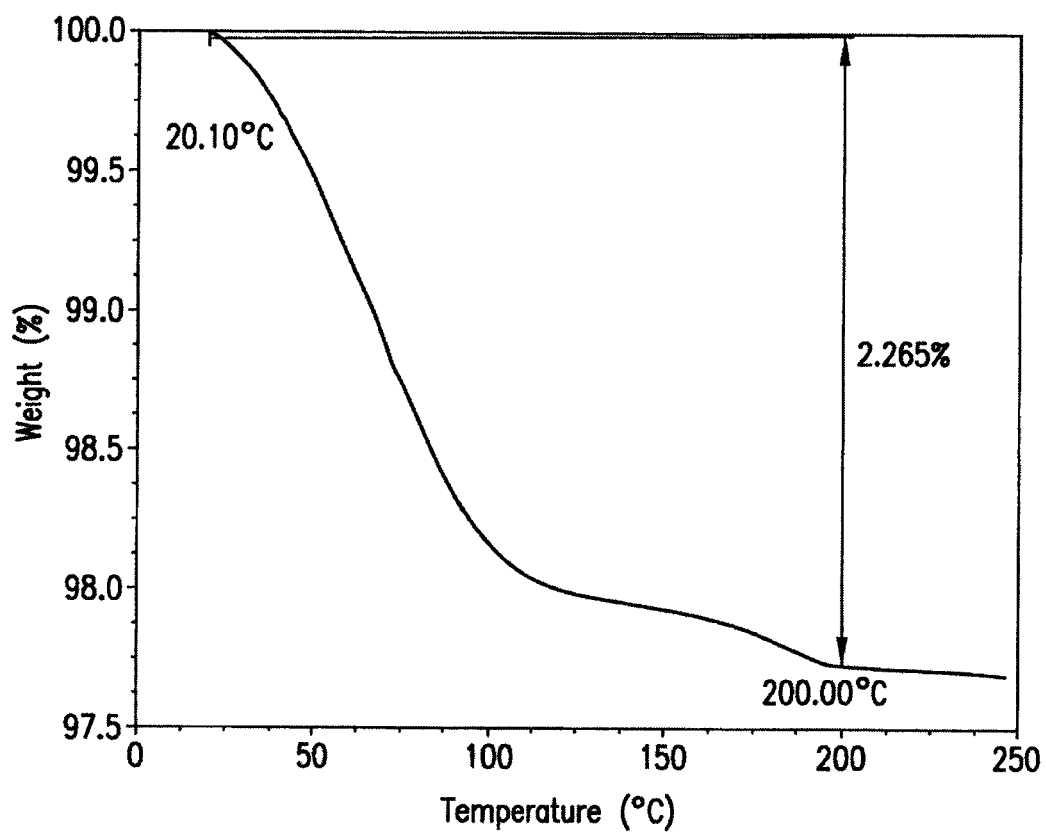
FIG. 3 illustrates a thermogravimetric analysis curve of Compound A Hydrate III.

In a fifth embodiment directed to Hydrate III, the hydrate is characterized by a thermogravimetric analysis as provided in FIG. 3.

Figure 4:
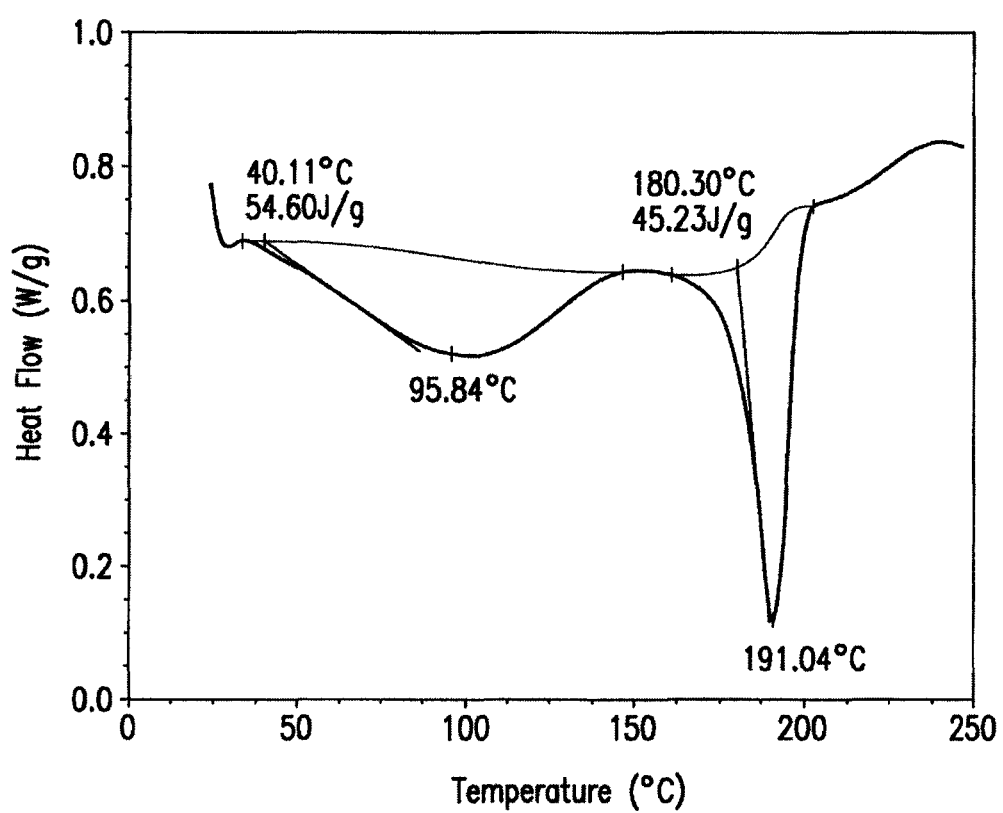
FIG. 4 illustrates a differential scanning calorimetry curve of Compound A Hydrate III.

In a sixth embodiment directed to Hydrate III, the hydrate is characterized by a differential scanning calorimetry curve as provided in FIG. 4.

Figure 5:
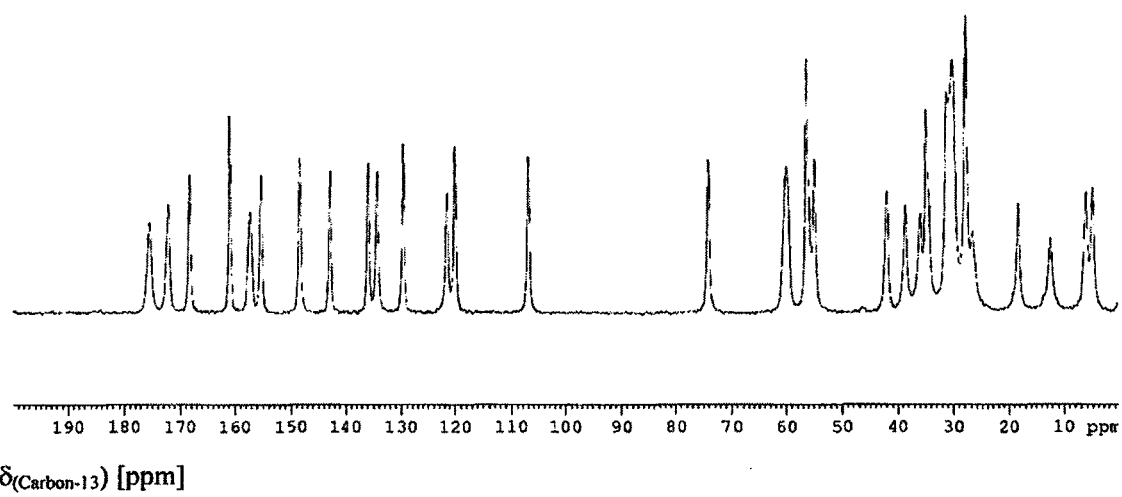
FIG. 5 illustrates a solid state C-13 CPMAS NMR for Compound A Hydrate III.

A seventh embodiment is directed to Hydrate III, where the hydrate is characterized by the solid state carbon-13 CPMAS NMR spectrum provided in FIG. 5.

A eighth embodiment is directed to Hydrate III, where the hydrate is characterized by a solid state carbon-13 CPMAS NMR comprising peaks at about 5.14, 6.31, 12.49, 18.35, 26.81, 28.03, 30.33, 31.27, 34.95, 35.99, 38.68, 42.01, 54.93, 56.39, 60.14, 74.20, 107.02, 120.11, 121.60, 129.73, 134.35, 135.95, 142.89, 148.47, 155.37, 157.32, 160.90, 168.32, 172.17, and 175.53 ppm.

Reference to "about" with respect to the solid state carbon-13 CPMAS NMR 2Θ values provided herein indicates ±0.1.

In another embodiment, Hydrate III is substantially pure. Reference to "substantially pure" means the particular form makes up at least 50% of the compound present. In different embodiments, Hydrate III makes up at least 75%, at least 85%, at least 90%, at least 95%, or about 94%-98% of Compound A present.

In additional aspects the Compound A is provided as a K or Na crystalline salt. These salts are hydrates.

Figure 6:
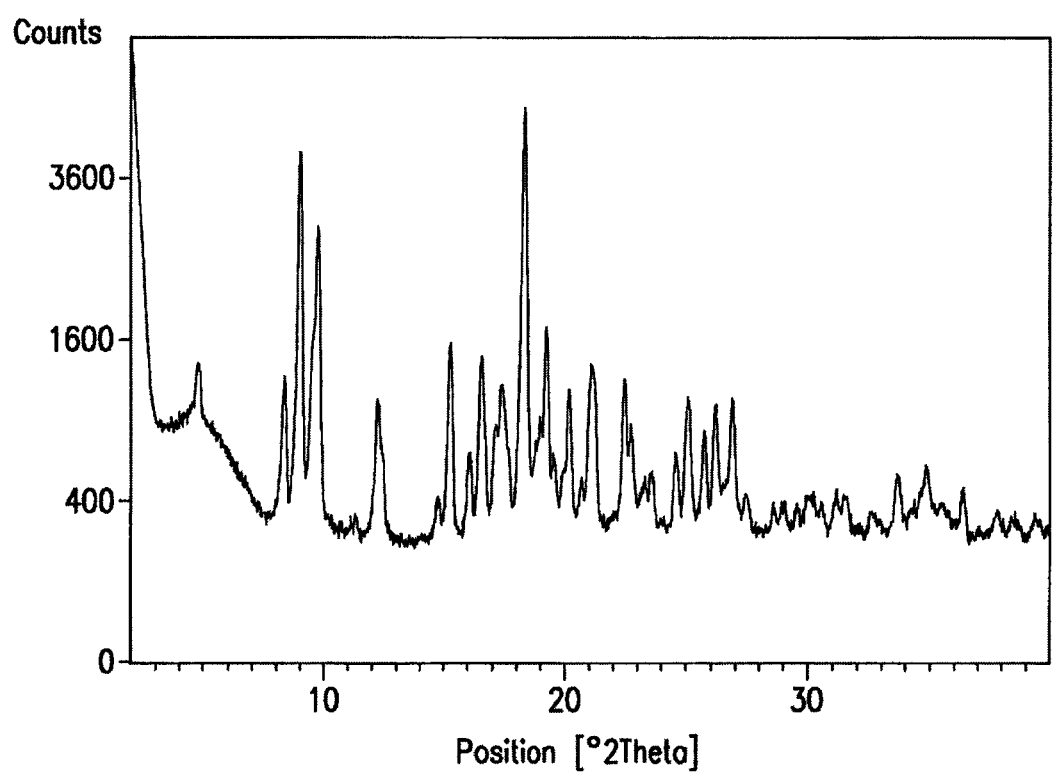
FIG. 6 illustrates an X-ray diffraction pattern of a crystalline Compound A Na-salt.

In a first embodiment directed to the Compound A crystalline Na salt, the compound is characterized by an X-ray powder diffraction pattern obtained using copper $K_\alpha$ radiation which comprises three or more characteristic peaks. Characteristic peeks are illustrated in FIG. 6.

In a second embodiment directed to the Compound A crystalline Na salt, the compound is characterized by an X-ray powder diffraction pattern obtained using copper $K_\alpha$ radiation which comprises 2Θ values in degrees of about 18.4, 9.1, and 9.8.

In a third embodiment directed to the Compound A crystalline Na salt, the compound is characterized by an X-ray powder diffraction pattern obtained using copper $K_\alpha$ radiation which comprises 2Θ values in degrees of about 18.4, 9.1, 9.8, 9.6, 19.3, 15.3 and 16.5.

In a fourth embodiment directed to the Compound A crystalline Na salt, the compound is characterized by an X-ray powder diffraction pattern obtained using copper $K_\alpha$ radiation which comprises 2Θ values in degrees of about 18.4, 9.1, 9.8, 9.6, 19.3, 15.3, 16.5, 22.5, 17.4, 20.2, 8.4, 21.3, 26.9, 4.8, and 26.2.

In another embodiment, Compound A crystalline Na salt is substantially pure. Reference to "substantially pure" means the particular form makes up at least 50% of the compound present. In different embodiments, Compound A crystalline Na salt makes up at least 75%, at least 85%, at least 90%, at least 95%, or about 94%-98% of Compound A present.

Figure 7:
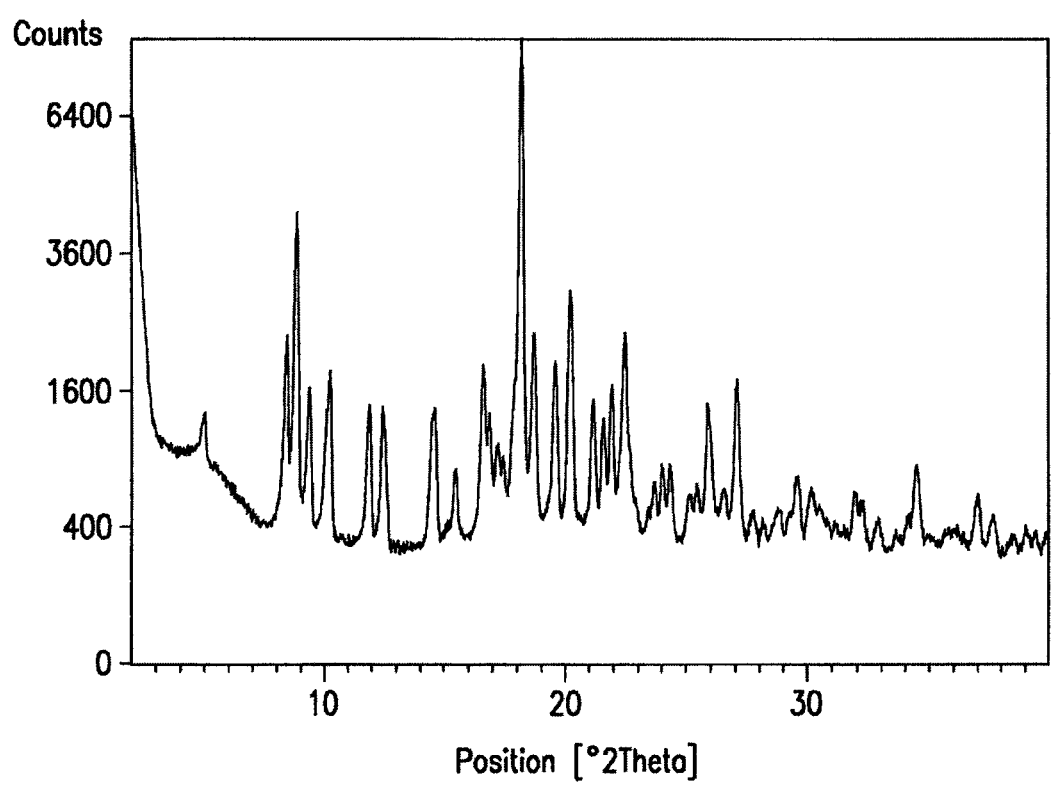
FIG. 7 illustrates an X-ray diffraction pattern of a crystalline Compound A K-salt.

In a first embodiment directed to the Compound A crystalline K salt, the compound is characterized by an X-ray powder diffraction pattern obtained using copper $K_\alpha$ radiation which comprises three or more characteristic peaks. Characteristic peeks are illustrated in FIG. 7.

In a second embodiment directed to the Compound A crystalline K salt, the compound is characterized by an X-ray powder diffraction pattern obtained using copper $K_\alpha$ radiation which comprises 2Θ values in degrees of about 18.2, 8.9, and 20.3.

In a third embodiment directed to the Compound A crystalline K salt, the compound is characterized by an X-ray powder diffraction pattern obtained using copper $K_\alpha$ radiation which comprises 2Θ values in degrees of about 18.2, 8.9, 20.3, 18.7 and 22.5.

In a fourth embodiment directed to the Compound A crystalline K salt, the compound is characterized by an X-ray powder diffraction pattern obtained using copper $K_\alpha$ radiation which comprises 2Θ values in degrees of about 18.2, 8.9, 20.3, 18.7, 22.5, 8.4, 19.6, 16.7, 27.1, 10.3, 21.9, 9.4, 21.2, 25.9, and 12.5.

In another embodiment, Compound A crystalline K salt is substantially pure. Reference to "substantially pure" means the particular form makes up at least 50% of the compound present. In different embodiments, Compound A crystalline K salt makes up at least 75%, at least 85%, at least 90%, at least 95%, or about 94%-98% of Compound A present.

Figure 8:
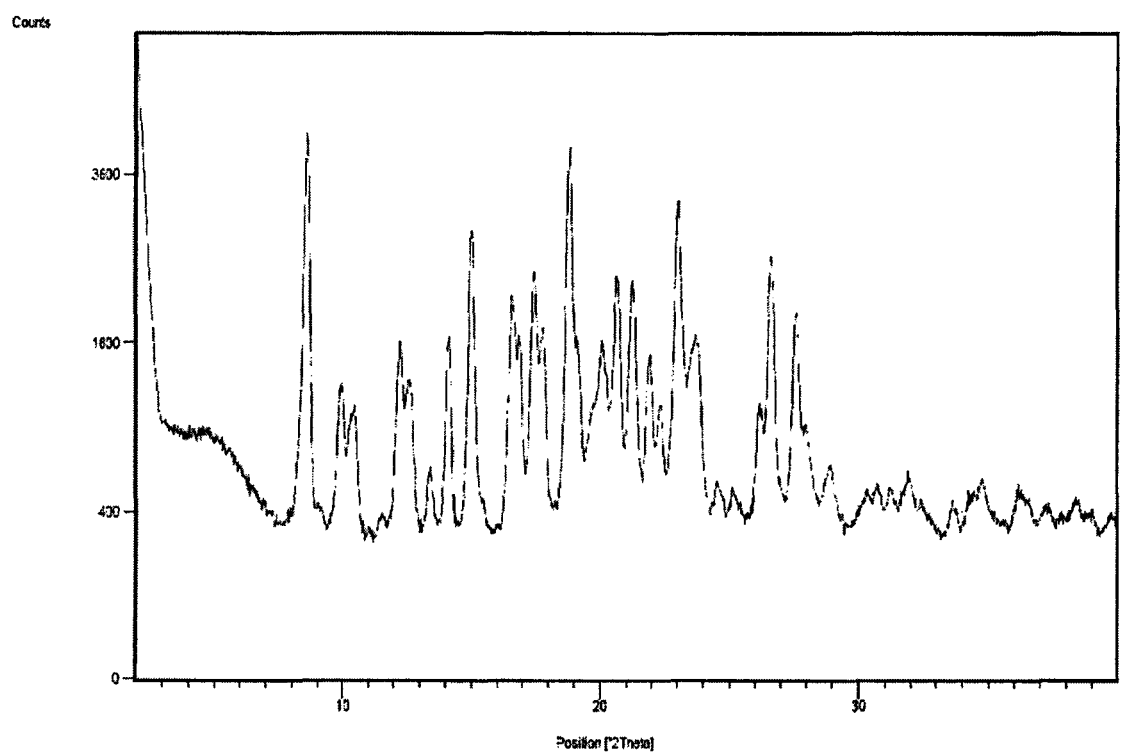
FIG. 8 illustrates an X-ray diffraction pattern of Compound A crystalline Hydrate 1.

In a first embodiment directed to Hydrate I, the hydrate is characterized by an X-ray powder diffraction pattern obtained using copper $K_\alpha$ radiation which comprises three or more characteristic peaks. Characteristic peeks are illustrated in FIG. 8.

In a second embodiment directed to Hydrate I, the hydrate is characterized by an X-ray powder diffraction pattern obtained using copper $K_\alpha$ radiation which comprises 2Θ values in degrees of about 8.6, 20.6, and 26.6.

In a third embodiment directed to Hydrate I, the hydrate is characterized by an X-ray powder diffraction pattern obtained using copper $K_\alpha$ radiation which comprises 2Θ values in degrees of about 8.6, 20.6, 26.6, 17.4, and 16.6.

In a fourth embodiment directed to Hydrate I, the hydrate is characterized by an X-ray powder diffraction pattern obtained using copper $K_\alpha$ radiation which comprises 2Θ values in degrees of about 8.6, 20.6, 26.6, 17.4, 16.6, 12.2, 21.2, 18.8, 15.0, 23.0, 14.1 and 16.9.

Figure 9:
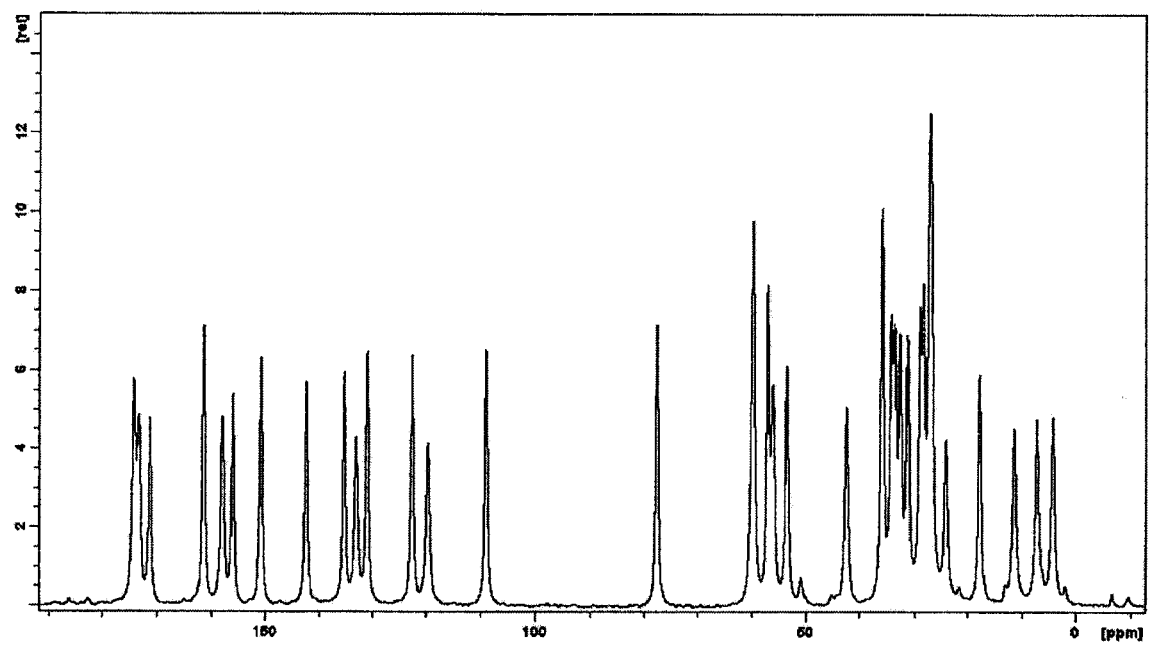
FIG. 9 illustrates a solid state C-13 CPMAS NMR for Compound A Hydrate I.

A seventh embodiment is directed to Hydrate I, where the hydrate is characterized by the solid state carbon-13 CPMAS NMR spectrum provided in FIG. 9.

A eighth embodiment is directed to Hydrate I, where the hydrate is characterized by a solid state carbon-13 CPMAS NMR comprising peaks at about 4.22, 7.23, 11.45, 17.79, 24.04, 26.95, 28.29, 31.15, 32.47, 32.47, 33.46, 34.03, 35.74, 42.32, 53.50, 56.05, 56.96, 77.49, 108.95, 119.65, 122.55, 131.05, 133.13, 135.38, 142.28, 150.78, 156.03, 157.99, 161.36, 171.40, 173.42, 174.30 ppm.

In another embodiment, Hydrate I is substantially pure. Reference to "substantially pure" means the particular form makes up at least 50% of the compound present. In different embodiments, Hydrate I makes up at least 75%, at least 85%, at least 90%, at least 95%, or about 94%-98% of Compound A present.

Figure 10:
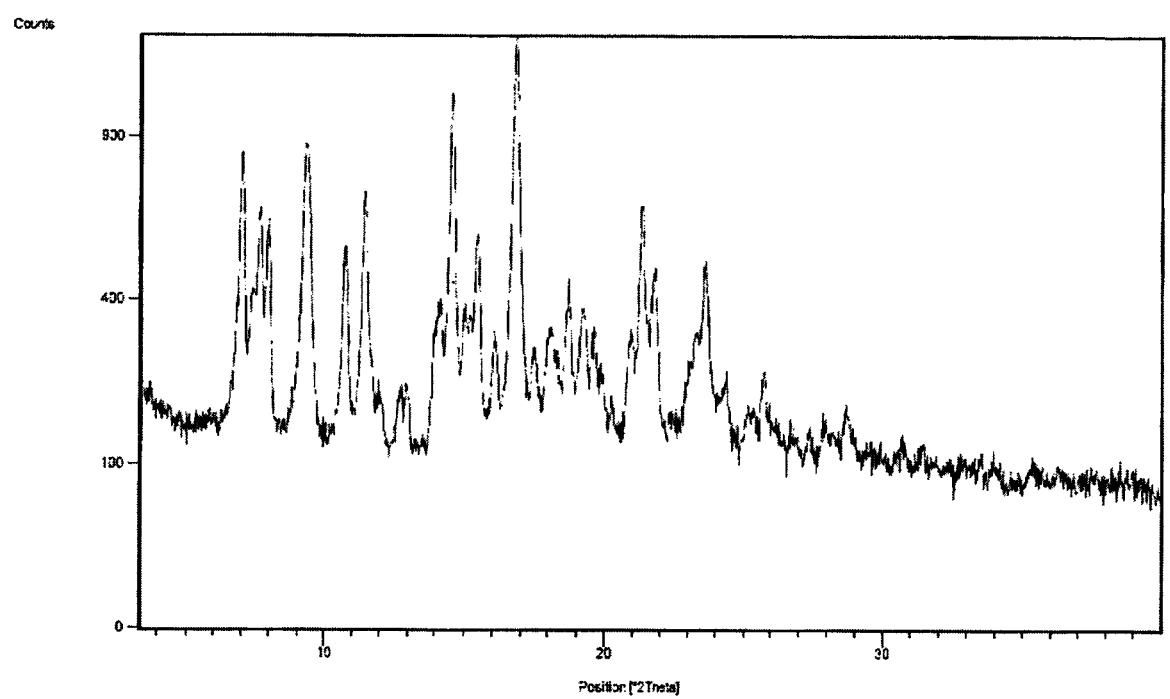
FIG. 10 illustrates an X-ray diffraction pattern of Compound A crystalline Hydrate IV.

In a first embodiment directed to Hydrate IV, the hydrate is characterized by an X-ray powder diffraction pattern obtained using copper $K_\alpha$ radiation which comprises three or more characteristic peaks. Characteristic peeks are illustrated in FIG. 10.

In a second embodiment directed to Hydrate IV, the hydrate is characterized by an X-ray powder diffraction pattern obtained using copper $K_\alpha$ radiation which comprises 2Θ values in degrees of about 14.7, 11.5, and 7.1.

In a third embodiment directed to Hydrate IV, the hydrate is characterized by an X-ray powder diffraction pattern obtained using copper $K_\alpha$ radiation which comprises 2Θ values in degrees of about 14.7, 11.5, 7.1, 9.3, and 15.6.

In a fourth embodiment directed to Hydrate IV, the hydrate is characterized by an X-ray powder diffraction pattern obtained using copper $K_\alpha$ radiation which comprises 2Θ values in degrees of about 14.7, 11.5, 7.1, 9.3, 15.6, 7.7, and 8.0.

Figure 11:
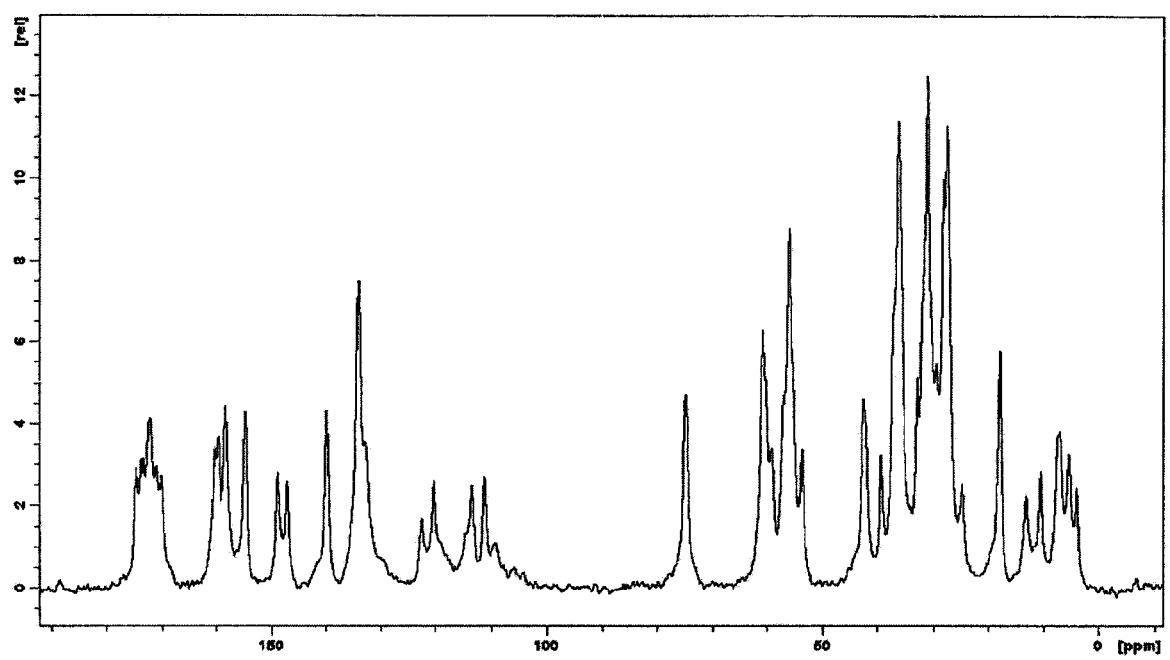
FIG. 11 illustrates a solid state C-13 CPMAS NMR for Compound A Hydrate IV.

A seventh embodiment is directed to Hydrate IV, where the hydrate is characterized by the solid state carbon-13 CPMAS NMR spectrum provided in FIG. 11.

A eighth embodiment is directed to Hydrate IV, where the hydrate is characterized by a solid state carbon-13 CPMAS NMR comprising peaks at about 3.90, 5.30, 6.99, 10.49, 13.13, 17.81, 24.73, 27.52, 28.14, 29.42, 31.02, 32.80, 36.08, 39.22, 42.45, 53.62, 55.93, 59.14, 60.76, 74.77, 109.22, 111.19, 11.38, 120.24, 122.50, 133.96, 139.74, 147.2, 148.90, 154.65, 158.25, 159.53, 160.12, 170.14, 171.05, 172.08, 173.47, and 174.46 ppm.

In another embodiment, Hydrate IV is substantially pure. Reference to "substantially pure" means the particular form makes up at least 50% of the compound present. In different embodiments, Hydrate IV makes up at least 75%, at least 85%, at least 90%, at least 95%, or about 94%-98% of Compound A present.

Figure 12:
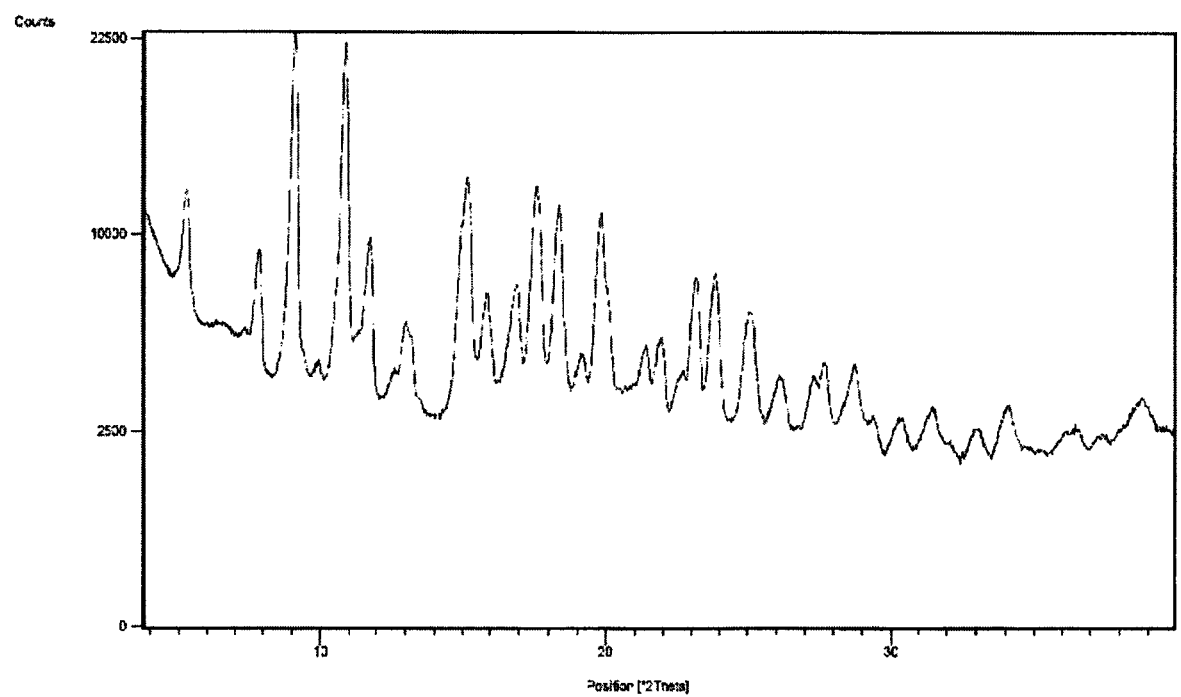
FIG. 12 illustrates an X-ray diffraction pattern of Compound A crystalline Hydrate V.

In a first embodiment directed to Hydrate V, the hydrate is characterized by an X-ray powder diffraction pattern obtained using copper $K_\alpha$ radiation which comprises three or more characteristic peaks. Characteristic peeks are illustrated in FIG. 12.

In a second embodiment directed to Hydrate V, the hydrate is characterized by an X-ray powder diffraction pattern obtained using copper $K_\alpha$ radiation which comprises 2Θ values in degrees of about 9.1, 18.3, and 19.8.

In a third embodiment directed to Hydrate V, the hydrate is characterized by an X-ray powder diffraction pattern obtained using copper $K_\alpha$ radiation which comprises 2Θ values in degrees of about 9.1, 18.3, 19.8, 15.2, and 23.2.

In a fourth embodiment directed to Hydrate V, the hydrate is characterized by an X-ray powder diffraction pattern obtained using copper $K_\alpha$ radiation which comprises 2Θ values in degrees of about 9.1, 18.3, 19.8, 15.2, 23.2, 10.9, 17.6 and 23.9.

Figure 13:
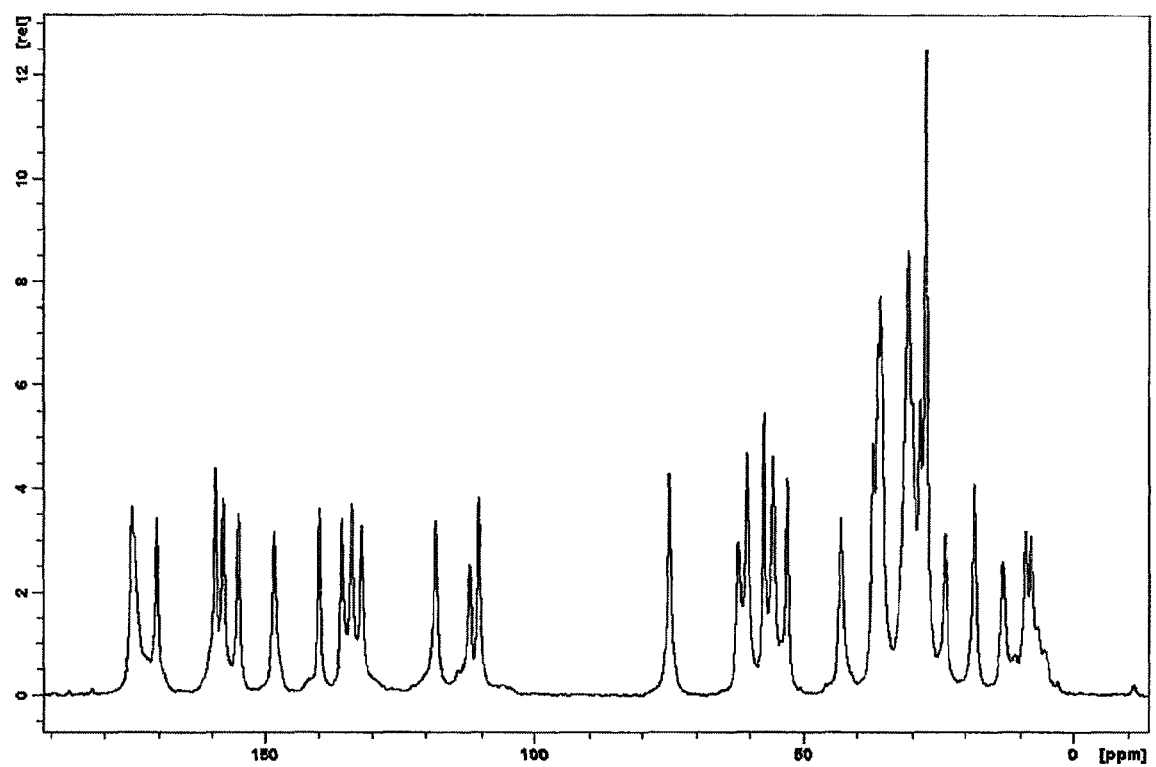
FIG. 13 illustrates a solid state C-13 CPMAS NMR for Compound A Hydrate V.

A seventh embodiment is directed to Hydrate V, where the hydrate is characterized by the solid state carbon-13 CPMAS NMR spectrum provided in FIG. 13.

A eighth embodiment is directed to Hydrate V, where the hydrate is characterized by a solid state carbon-13 CPMAS NMR comprising peaks at about 7.86, 8.92, 13.10, 18.31, 23.72, 27.44, 28.47, 30.77, 35.79, 36.25, 37.15, 37.15, 42.95, 53.13, 55.67, 57.31, 60.47, 62.06, 75.09, 110.59, 112.24, 118.32, 132.18, 134.05, 135.83, 139.88, 148.30, 155.19, 157.97, 159.41, 170.31 and 175.20 ppm.

In another embodiment, Hydrate V is substantially pure. Reference to "substantially pure" means the particular form makes up at least 50% of the compound present. In different embodiments, Hydrate V makes up at least 75%, at least 85%, at least 90%, at least 95%, or about 94%-98% of Compound A present.

Figure 14:
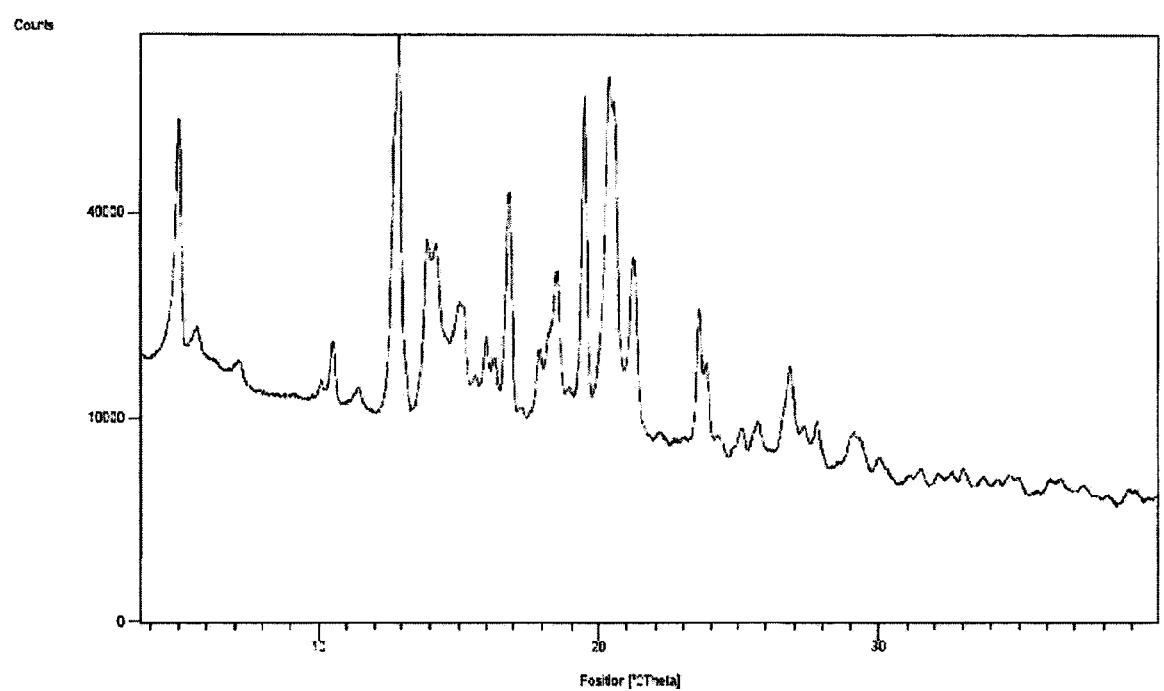
FIG. 14 illustrates an X-ray diffraction pattern of Compound A crystalline Hydrate VI.

In a first embodiment directed to Hydrate VI, the hydrate is characterized by an X-ray powder diffraction pattern obtained using copper $K_\alpha$ radiation which comprises three or more characteristic peaks. Characteristic peeks are illustrated in FIG. 14.

In a second embodiment directed to Hydrate VI, the hydrate is characterized by an X-ray powder diffraction pattern obtained using copper $K_\alpha$ radiation which comprises 2Θ values in degrees of about 20.5, 12.8, and 19.4.

In a third embodiment directed to Hydrate VI, the hydrate is characterized by an X-ray powder diffraction pattern obtained using copper $K_\alpha$ radiation which comprises 2Θ values in degrees of about 20.5, 12.8, 19.4, 21.2, and 16.8.

In a fourth embodiment directed to Hydrate VI, the hydrate is characterized by an X-ray powder diffraction pattern obtained using copper $K_\alpha$ radiation which comprises 2Θ values in degrees of about 20.5, 12.8, 19.4, 21.2, 16.8, 13.9, 5.0, 18.5, 23.7, and 26.8.

Figure 15:
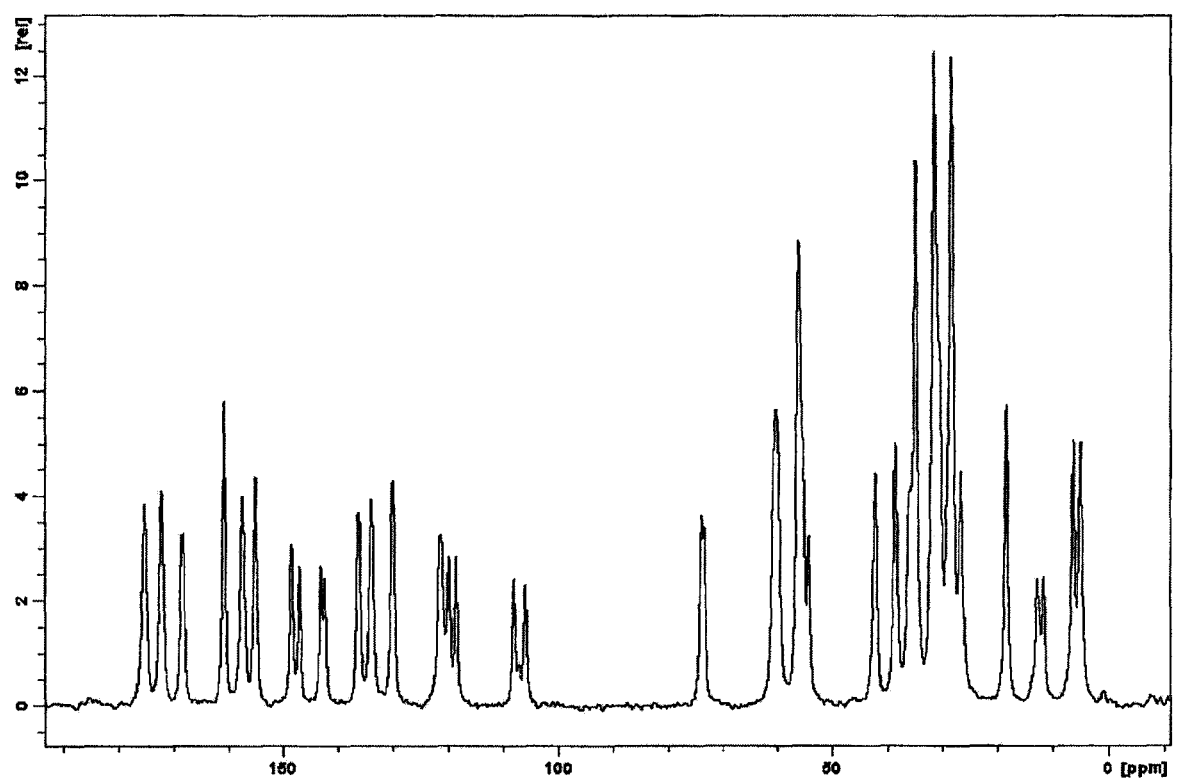
FIG. 15 illustrates a solid state C-13 CPMAS NMR for Compound A Hydrate VI.

A seventh embodiment is directed to Hydrate VI, where the hydrate is characterized by the solid state carbon-13 CPMAS NMR spectrum provided in FIG. 15.

A eighth embodiment is directed to Hydrate VI, where the hydrate is characterized by a solid state carbon-13 CPMAS NMR comprising peaks at about 4.87, 6.24, 11.70, 12.85, 18.36, 26.55, 28.31 m 31.51, 34.98, 38.47, 42.09, 54.27, 56.12, 60.10, 73.49, 73.97, 105.91, 108.04, 118.39, 119.75, 121.33, 129.96, 133.87, 136.13, 142.26, 142.97, 146.85, 148.36, 154.97, 157.32, 160.71, 168.23, 172.21 and 175.34 ppm.

In another embodiment, Hydrate VI is substantially pure. Reference to "substantially pure" means the particular form makes up at least 50% of the compound present. In different embodiments, Hydrate VI makes up at least 75%, at least 85%, at least 90%, at least 95%, or about 94%-98% of Compound A present.

Another aspect is directed to a method of making Hydrate III from Compound A involving the use of acetone/water and drying. Different ratios of acetone/water can be employed. In different embodiments, the acetone to water ratio is between 80:20 v/v acetone to water and 0:100 v/v acetone to water. In additional embodiments, the acetone to water ratio is 65:35, 50:50, about 65:35, or about 50:50; and/or Hydrate II or Hydrate IV of Compound A is used as the starting point to make Hydrate III; and/or the compound is initially dissolved in acetone.

Reference to about with respect to acetone:water ratio indicates a range of ±10 for each component. For example, "about" for the ratio 65:35, indicates acetone can vary from 55-75.

In an embodiment, crude (Hydrate II) is dissolved in acetone. Water is added to the process to bring the solvent composition to 85:15 acetone:water. The process is then seeded to start crystallization, and water is then added to improve the yield and the final solvent composition is 50:50 acetone:water.

Isotopic Enrichment

The atoms in a compound described herein may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds described herein. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples.

Isotopically-enriched compounds described herein can be prepared without undue experimentation by conventional techniques well known to those skilled in the art or by processes analogous to those described in the Schemes and Examples provided herein using appropriate isotopically-enriched reagents and/or intermediates.

Administration and Compositions

Pharmaceutically acceptable salts are suitable for administration to a patient, preferably, a human. Suitable salts include acid addition salts which may, for example, be formed by mixing a solution of a compound with a solution of a pharmaceutically acceptable acid such as hydrochloric acid, sulfuric acid, acetic acid, trifluoroacetic acid, or benzoic acid. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

Compound A can be administered to a patient infected with HCV. The term "administration" and variants thereof (e.g., "administering" a compound) means providing the compound to the individual in need of treatment. When a compound is provided in combination with one or more other active agents (e.g., antiviral agents useful for treating HCV infection), "administration" and its variants are each understood to include concurrent and sequential provision of the compound or salt and other agents.

As used herein, the term "composition" is intended to encompass a product comprising the specified ingredients, as well as any product which results, directly or indirectly, from combining the specified ingredients.

By "pharmaceutically acceptable" is meant the ingredients of the pharmaceutical composition are compatible with each other and are suitable to the recipient thereof.

The term "subject" (alternatively referred to herein as "patient") as used herein refers to an animal, preferably a mammal, most preferably a human, who is the object of treatment, observation or experiment.

The term "effective amount" indicates a sufficient amount to exert a therapeutic or prophylactic effect. For a patient infected with HCV, an effective amount is sufficient to achieve one or more of the following effects: reduce the ability of HCV to replicate, reduce HCV load, and increase viral clearance. For a patient not infected with HCV, an effective amount is sufficient to achieve one or more of the following: a reduced susceptibility to HCV infection, and a reduced ability of the infecting virus to establish persistent infection for chronic disease.

For the purpose of inhibiting HCV NS3 protease and treating HCV infection and/or reducing the likelihood or severity of symptoms of HCV infection, the compounds, optionally in the form of a salt, can be administered by means that produces contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice.

Compounds can, for example, be administered by one or more of the following routes: orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and pharmaceutically-acceptable carrier (e.g., a carrier suitable for administration to a human patient), adjuvants and vehicles. Liquid preparations suitable for oral administration (e.g., suspensions, syrups, elixirs and the like) can employ media such as water, glycols, oils, alcohols and the like. Solid preparations suitable for oral administration (e.g., powders, pills, capsules and tablets) can employ solid excipients as such starches, sugars, kaolin, lubricants, binders, disintegrating agents and the like. Parenteral compositions typically employ sterile water as a carrier and optionally other ingredients, such as solubility aids. Injectable solutions can be prepared, for example, using a carrier comprising a saline solution, a glucose solution or a solution containing a mixture of saline and glucose. Further guidance for methods suitable for use in preparing pharmaceutical compositions is provided in *Remington: The Science and Practice of Pharmacy,* $21^{th}$ edition (Lippincott Williams & Wilkins, 2006).

Therapeutic compounds can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, 500, and 750 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Other embodiments of the present invention include the following:

(a) A pharmaceutical composition comprising an effective amount of Compound A and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors, NS5A inhibitors, and HCV NS5B polymerase inhibitors.

(d) A pharmaceutical combination that is (i) Compound A and (ii) a second therapeutic agent selected from the group consisting of HCV antiviral agents, immunomodulators, and anti-infective agents; wherein Compound A and the second therapeutic agent are each employed in an amount that renders the combination effective for inhibiting HCV replication, for treating HCV infection and/or reducing the likelihood or severity of symptoms of HCV infection.

(e) The combination of (d), wherein the HCV antiviral agent is an antiviral selected from the group consisting of HCV protease inhibitors, NS5A inhibitors, and HCV NS5B polymerase inhibitors.

(f) A method of inhibiting HCV replication in a subject in need thereof which comprises administering to the subject an effective amount of Compound A.

(g) A method of treating HCV infection and/or reducing the likelihood or severity of symptoms of HCV infection in a subject in need thereof which comprises administering to the subject an effective amount of Compound A.

(h) The method of (g), wherein the compound is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors, NS5A inhibitors and HCV NS5B polymerase inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

The present invention also includes a compound of the present invention for use in medicine; or for use in (i) a medicament, (ii) in the preparation of a medicament, for (a) inhibiting HCV replication or (b) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

HCV Inhibitory Activity

The ability of a compound to inhibit HCV NS3 activity, HCV replicon activity, and HCV replication activity can be evaluated using techniques well-known in the art. (See, for example, Carroll et al., *J. Biol. Chem.* 278:11979-11984, 2003.)

One such assay is a HCV NS3 protease time-resolved fluorescence (TRF) assay as described below and in Mao et al., *Anal. Biochem.* 373:1-8, 2008 and Mao et al., WO 2006/102087. A NS3 protease assay can be performed, for example, in a final volume of 100 µl assay buffer containing 50 mM HEPES, pH 7.5, 150 mM NaCl, 15% glycerol, 0.15% TRITON X-100, 10 mM DTT, and 0.1% PEG 8000. NS3 and NS4A are pre-incubated with various concentrations of inhibitors in DMSO for 30 minutes. The reaction is initiated by adding the TRF peptide substrate (final concentration 100 nM). NS3 mediated hydrolysis of the substrate is quenched after 1 hour at room temperature with 100 µl of 500 mM MES, pH 5.5. Product fluorescence is detected using either a VICTOR V2 or FUSION fluorophotometer (Perkin Elmer Life and Analytical Sciences) with excitation at 340 nm and emission at 615 nm with a 400 µs delay. Testing concentrations of different enzyme forms are selected to result in a signal to background ratio (S/B) of 10-30. $IC_{50}$ values are derived using a standard four-parameter fit to the data. K, values are derived from $IC_{50}$ values using the following formula, $$IC_{50}=K_i(1+[S]/K_M), \qquad \text{Eqn (1)},$$

where [S] is the concentration of substrate peptide in the reaction and $K_M$ is the Michaelis constant. See P. Gallinari et al., 38 BIOCHEM. 5620-32 (1999); P. Gallinari et al., 72 J. VIROL. 6758-69 (1998); M. Taliani et al., 240 ANAL. BIOCHEM. 60-67 (1996); and Mao et al., *Analytical Biochemistry* 373: 1-8, (2008).

Abbreviations

BOC: t-Butoxycarbonyl
Cbz: Benzyloxycarbonyl
CDI: 1,1'-Carbonyldiimidazole
CIP: 2-Chluoro-1-methylpyridinium iodide
CPME: Cyclopentyl methyl ether
DABO: 1,4-Diazabicyclo[2.2.2.]octane
DBA saltdibenzylamine
DBU: 1,8-Diazobicyclo[5.4.0]undec-7-ene
DCC: N,N-Dicyclohexylcarbodiimide
DIC: N,N'-diisopropylcarbodiimide
DIPEA: Diisopropylethylamine
DMAc: N,N-Dimethylacetamide
DMF: N,N-Dimethylformamide
DMPU: N,N-dimethylpropyleneurea
DMSO: Dimethylsulfoxide
EDC: 1-Ethyl-3-(3-dimethylaminopropyl) carbodiimide
EtOAc: Ethyl acetate
Fmoc: 9-Fluorenylmethyloxycarbonyl
HATU: 2-(1H-7-Azabenzotriazole-1-yl)-1,1,3,3-tetramethyluronium hexafluorophosphate
HOAT: 1-Hydroxy-7-azabenzotriazole
HOBT: 1-Hydroxybenzotriazole
HOPO: 2-Hydroxypyridine-N-oxide
HOSu: N-hydroxysuccinimide
IPA: Isopropanol IPAc: Isopropyl acetate
MTBE: t-butyl methyl ether
MsOH and MSA: $CH_3SO_3H$ or methanesulfonic acid
Moz: p-Methoxybenzyloxycarbonyl
Msz: 4-Methylsulfinylbenzyloxycarbonyl
NMP: N-Methylpyrrolidone
PFP: pentafluorophenol
T3P: propylphosphonic anhydride
TBA: t-butyl amine
TEA: Triethylamine
THF: Tetrahydrofuran
pTSA and TsOH are each abbreviations for p-toluenesulfonic acid.

EXAMPLES

The examples provided below are intended to illustrate the invention and its practice. Unless otherwise provided in the claims, the examples are not to be construed as limitations on the scope or spirit of the invention.

Example 1

Preparation of 2-[2-(3-Chloro-propyl)-cyclopropyl]-4,4,5,5-tetramethyl-[1,3,2]dioxaborolane (Compound 3)

Compound 2 can be prepared as described by Shirakawa et al. *Synthesis* 11:1814-1820, 2004.)

Compound 3 was produced as follows: To a 5 L flask equipped with a nitrogen inlet, mechanical stirrer, dropping funnel and thermocouple under $N_2$ was added 800 mL dichloromethane and 800 mL of a 1 M diethylzinc solution in heptane (0.8 mol, 1.07 equiv). The solution was cooled with an ice bath to an internal temperature of 3° C. To the flask was then added from the dropping funnel a solution of 57.6 mL trifluoroacetic acid (0.748 mol, 1.0 equiv) in 200 mL dichloromethane over 1 hour, keeping the internal temperature below 10° C. The resulting suspension was stirred for 30 min at 3° C. To the flask was then added 72.4 mL diiodomethane (0.897 mol, 1.2 equiv) in a single portion. After stirring at 3° C. for 30 min, 172 mL of 2 (0.748 mol, 1.0 equiv) was added to the solution in a single portion. The flask was then allowed to warm to room temperature and a white precipitate began to form. After 3 hours, GC analysis indicated the reaction was at 90% conversion. The suspension was aged for an additional 17 hours or until complete consumption of 2 is observed. At that point, 800 mL of 1 M HCl (0.8 mol, 1.07 equiv) was added and a ±5° C. exotherm was observed. The biphasic mixture was stirred for 30 min to dissolve the precipitated solids and the organic layer was separated. Extraction of the aqueous layer with 200 mL dichloromethane, washing of the combined organic layers with 500 mL brine and concentration in vacuo gave 194 g of 3 as a yellow oil (74 wt % in DCM). $^1$H NMR (400 MHz, $CDCl_3$) δ 3.59 (t, 2H, J=6.7 Hz), 1.90 (pent, 2H, J=7.1 Hz), 1.49 (sext, 1H, J=7.0 Hz), 1.36 (sext, 1H, J=7.0 Hz), 1.23 (s, 12H), 0.93 (m, 1H), 0.71 (m, 1H), 0.44 (m, 1H), −0.35 (dt, 1H, J=9.4, 5.7 Hz); $^{13}$C NMR (100 MHz, $CDCl_3$) δ 82.82, 44.74, 32.67, 32.22, 24.64, 17.22, 11.24, 0.5 (bs); GC: HP1 (30 m×0.32 mm; 0.25 μm), 25 psi, 200° C. front inlet. 5 min @ 50° C., ramp 25/min to 250° C. then hold for 4 min, $t_r$(2)=9.78 min, $t_r$(3)=10.08 min.

Example 2

Preparation of 2-(3-Chloro-propyl)-cyclopropanol (Compound 4)

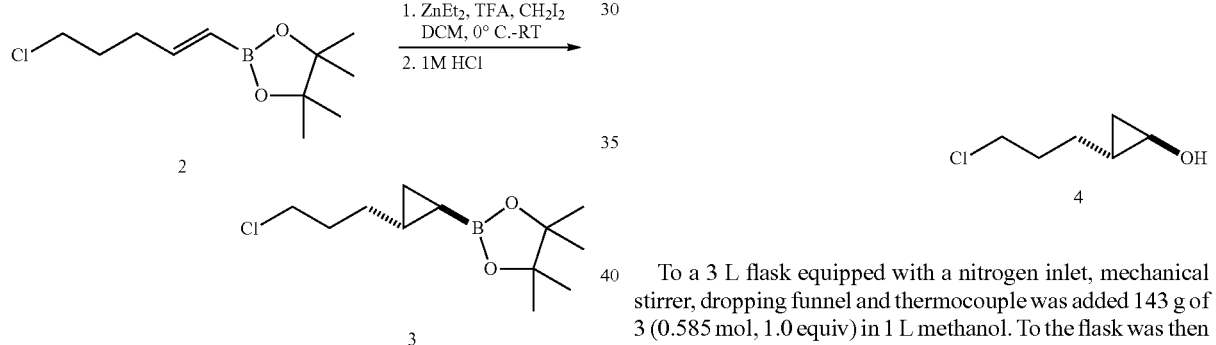

To a 3 L flask equipped with a nitrogen inlet, mechanical stirrer, dropping funnel and thermocouple was added 143 g of 3 (0.585 mol, 1.0 equiv) in 1 L methanol. To the flask was then added from the dropping funnel 58.5 mL of 10 M sodium hydroxide (0.585 mol, 1.0 equiv) over 30 min, while the internal temperature was maintained below 10° C. with external cooling. After stirring for 30 min, 120 mL of 30 wt % hydrogen peroxide solution (1.17 mol, 2 equiv) was slowly added from the dropping funnel over 1 hour, keeping the internal temperature below 10° C. Upon completion of the addition, the resulting colorless slurry was then stirred at ambient temperature for 30 min or until complete consumption of 3 was observed by GC. 2 M HCl (375 mL) was added from the dropping funnel over 30 min, keeping the internal temperature below 10° C. To this clear yellow solution was then slowly added 500 mL of a 1 M solution of $Na_2SO_3$ from the dropping funnel, keeping the internal temperature below 10° C. The resulting suspension was then filtered and extracted 3×200 mL MTBE. Concentration followed by silica gel column chromatography (6:4 hexane:ethyl acetate), to remove pinacol, gave 60.6 g of product 4 as a clear oil (90 wt %). $^1$H NMR (400 MHz, $CDCl_3$) δ 3.62 (t, 2H, J=6.6 Hz), 3.27 (dt, 1H, J=6.3, 2.6 Hz), 1.89 (pent, 2H, J=6.8 Hz), 1.85 (bs, OH), 1.43 (sext, 1H, J=7.0 Hz), 1.28 (sext, 1H, J=7.0 Hz), 0.94 (m, 1H), 0.75 (m, 1H), 0.38 (q, 1H, J=6.0 Hz); $^{13}$C NMR (100 MHz, $CDCl_3$) δ 52.21, 44.69, 31.91, 28.69, 19.69, 14.15; GC: HP1 (30 m×0.32 mm; 0.25 μm), 25 psi, 200° C.

front inlet. 5 min @ 50° C., ramp 25/min to 250° C. then hold for 4 min, $t_r(3)$=10.08 min, $t_r(4)$=7.15 min.

Example 3

Preparation of 2-Pent-4-ynyl-cyclopropanol (rac-Compound 5)

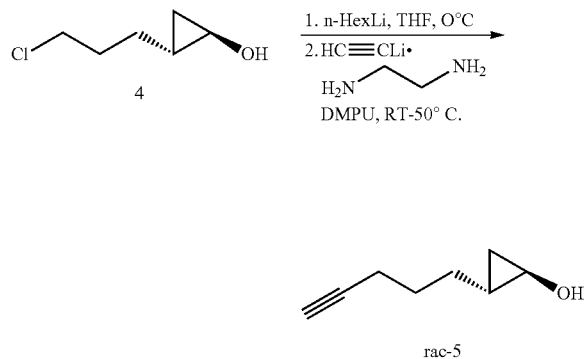

rac-5

To a 2-neck 15-mL flask equipped with a temperature probe, $N_2$ inlet, and septum was added 1 g of 4 (7.28 mmol, 1.0 equiv) and 3.0 mL THF. The solution was cooled to an internal temperature of 0° C. with an ice bath. To this solution was added 2.95 mL of 33 wt % n-Hexyllithium (7.28 mmol, 1.0 equiv) slowly via syringe pump over 1 hour. Internal temperature rose to 6.8° C. and solution became yellow. In a separate 3-neck 100-mL flask equipped with a temperature probe, $N_2$ inlet, and septum 0.82 g of lithium acetylide-ethylenediamine complex (8.01 mmol, 1.1 equiv) was slurried in 5.0 mL of DMPU at room temperature. To this room temperature slurry, the cold solution of the deprotonated cyclopropanol was transferred via cannula over 5 min. After the addition, the brown mixture was heated to an internal temperature of 52° C. with a heating mantle for 3 hours or until greater than 98% conversion was observed by GC. The brown mixture was cooled with an ice bath to 3° C. and then the ice bath was removed to prevent freezing. To this was slowly added 17.5 mL of 0.5 N HCl and an ice bath was applied to maintain an internal temperature below 21° C. The mixture was then diluted with 10 mL MTBE and 5 mL of water before transfer to a separatory funnel and removal of the aqueous layer. The aqueous layer was extracted once with 15 mL MTBE and then the combined organic layers were washed with 20 mL water followed by 20 mL brine. The organic layer was then concentrated in vacuo to afford 1.27 g of rac-5 as a yellow oil (72 wt %). $^1$H NMR (400 MHz, CDCl$_3$) δ 3.24 (dt, 1H, J=2.6, 5.3 Hz), 2.25 (dt, 2H, J=2.6, 7.6 Hz), 1.96 (t, 1H, J=2.6 Hz), 1.92 (s, 1H, OH), 1.64 (pent, 2H, J=7.3 Hz), 1.38 (sext, 1H, J=6.9 Hz), 1.24 (sext, 1H, J=6.9 Hz), 0.93 (m, 1H), 0.72 (m, 1H), 0.35 (q, 1H, J=6.0 Hz); $^{13}$C NMR (100 MHz, CDCl$_3$) δ 84.49, 68.37, 52.45, 30.50, 27.74, 20.17, 18.01, 14.25; GC: HP1 (30 m×0.32 mm; 0.25 µm), 25 psi, 200° C. front inlet. 5 min @ 50° C., ramp 25° C./min to 250° C. then hold for 4 min, $t_r(4)$=7.15 min, $t_r$(rac-5)=6.72 min.

Example 4

Preparation of Acetic Acid racemic trans-2-pent-4-ynyl-cyclopropyl ester (rac-Compound 6)

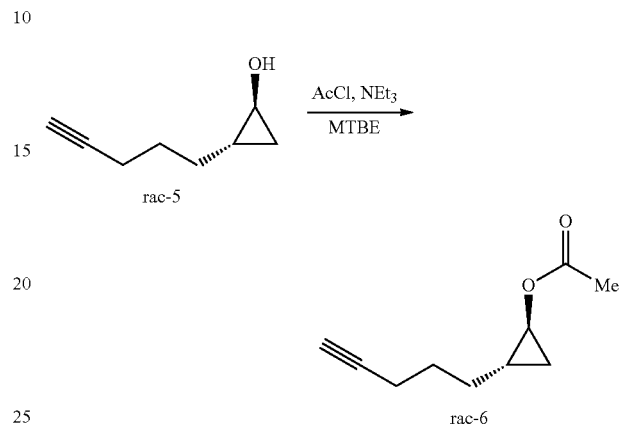

To a 5 L flask equipped with a nitrogen inlet, mechanical stirrer, dropping funnel and thermocouple under $N_2$ was added 31.2 g of rac-5 (251 mmol, 1.0 equiv), 350 mL of MTBE and 45.5 mL of triethylamine (327 mmol, 1.3 equiv) prior to cooling the solution in an acetone/ice bath to an internal temp of <5° C. To the solution was added from the dropping funnel 23.7 mL acetyl chloride (301 mmol, 1.1 equiv) over a 30 min period while maintaining the internal temp <10° C. The resulting slurry was then warmed to room temperature and aged for 2 hours. The reaction mixture was then diluted with 200 mL of water. The organic layer was washed with 200 mL of 2 N HCl and then with 300 mL of sat. NaHCO$_3$ prior to drying over MgSO$_4$. The solvent was removed in vacuo to give 41.8 g of rac-6. $^1$H NMR (400 MHz, CDCl$_3$) δ 3.84 (dt, 1H, J=6.7, 2.9 Hz), 2.25 (dt, 2H, J=2.7, 7.0 Hz), 2.03 (s, 3H), 1.95 (t, 1H, J=2.6 Hz), 1.67 (m, 2H), 1.39 (m, 2H), 1.01 (m, 1H), 0.89 (m, 1H), 0.57 (q, 1H, J=6.5 Hz); $^{13}$C NMR (100 MHz, CDCl$_3$) δ 171.60, 84.15, 68.47, 54.20, 30.12, 27.40, 20.85, 17.92, 17.83, 11.81; GC: Restek RT-Bdex SA (30 m×0.25 mm×0.25 µm), 60 cm/s linear velocity, 20:1 split, 120° C. isothermal, $t_r(5)$=25.0, 29.6 min, $t_r(6)$=17.1, 17.5 min.

Example 5

Preparation of (1R,2R)-2-Pent-4-ynyl-cyclopropanol (ent-Compound 5)

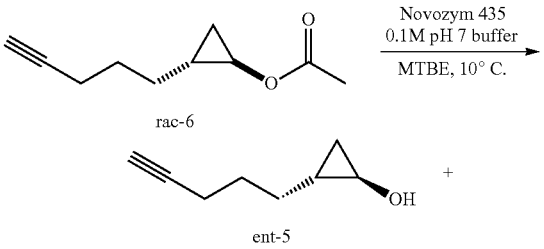

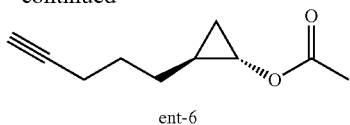

ent-6

To a 1-L flask equipped with an overhead stirrer and temperature probe was added a 60 wt % solution of rac-6 in MTBE (44.8 g, 0.27 mol) and an additional 730 ml of MTBE that had been saturated with aqueous 0.1 M pH 7 phosphate buffer, giving a final solution concentration of rac-6 of 60 g/l. The flask was placed in an ice bath to maintain an internal temperature of approximately 10° C. throughout the hydrolysis reaction, which was initiated by the addition of 730 mg Novozym 435. The reaction was aged at 10° C. for approximately 4 hours until conversion had reached 41%, at which point the ee of ent-5 was 96%. The reaction mixture was then filtered through a 150-ml medium-pore glass filter funnel and the solid immobilized enzyme was washed three times with 80 ml MTBE. The resulting MTBE solution was then solvent switched to heptane. The mixture in heptane (39.2 kg, approximately 50 L) was applied to a Biotage Flash 400 L cartridge (40×60 cm, 40 kg silica gel, 60 angstrom, 40-63 um) and eluted sequentially with 165 L of 2.5:97.5, 75 L of 10:90, and 330 L of 25:75 EtOAc/heptane (v/v). After the mixture was applied to the column, 18 L fractions were taken. The rich cut fractions of the alcohol ent-5 were located by TLC (silica, 20% EtOAc/heptane) and then analyzed by GC(HP-1, 30 m×320 um×0.25 um film, 9.14 psi constant He pressure, 15:1 split, 50° C. for 5 min then 25 deg/min to 275° C. and hold 5 min, RT of alcohol 8.8 min). Fractions 15-21 were concentrated to give 3.48 kg (80 wt %, 92% ee) of the desired ent-5 (Compound 7).

GC: Restek RT-Bdex SA (30 m×0.25 mm×0.25 μm), 60 cm/s linear velocity, 20:1 split, 120° C. isothermal, $t_r(5)$=25.0, 29.6 min, $t_r(6)$=17.1, 17.5 min.

Example 6

Preparation of (S)-3,3-Dimethyl-2-((1R,2R)-2-pent-4-ynyl-cyclopropoxycarbonylamino)-butyric acid (Compound 8)

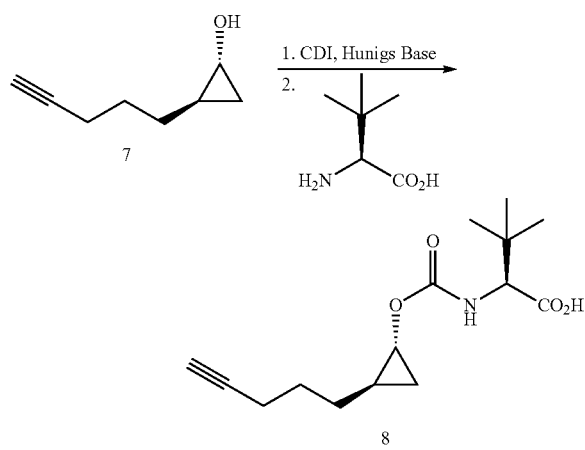

To a 50 L round bottom flask equipped with a mechanical stirrer, thermocouple and reflux condenser was added Compound 7 (3.477 kg @ 81 wt % by NMR, 92% ee) and 14.1 L (5 L/kg) of Hunigs base. To the resulting homogeneous solution was added CDI portion wise as a solid while maintaining the internal temperature between 21-25° C. The resulting slurry was aged at room temperature for 1 hour. To the slurry was added L-tert-leucine as a solid and the reaction mixture was heated to an internal temperature of 95° C. for 2.5 hours. The reaction mixture was cooled to room temperature and diluted with 17 L of water. The mixture was aged for 30 min to dissolve all the solids and then transferred to a 100 L cylindrical extractor. The aqueous layer was then washed with 12 L of MTBE. The aqueous layer was washed with 8 L of MTBE. The resulting aqueous layer was pH adjusted with concentrated HCl to a final pH of 1.5-2.0. The biphasic mixture was extracted with MTBE (2×12 L) and the combined organic phase was washed with 6 L of water followed by 5 L of brine.

The MTBE layer was then transferred via vacuum into a 50 L round bottom flask equipped with a mechanical stirrer, thermocouple, and batch concentrator and the solvent was removed under reduced pressure keeping the internal temperature of the batch <20° C. during the distillation. The solvent was then switched to cyclopentyl methyl ether (CPME) by flushing with ~5 L of CPME and then diluted to a final volume of ~20 L. This material was used in the next reaction without further purification.

An analytical sample was obtained by silica gel chromatography as a colorless oil: $^1$H NMR (CDCl$_3$, 400 MHz) δ 0.54 (q, 1H, J=6.4 Hz), 0.83 (m, 1H), 0.99 (m, 1H), 1.01 (s, 9H), 1.40 (m, 2H), 1.67 (m, 214), 1.94 (t, 1H, J=2.6 Hz), 2.23 (m, 2H), 3.77 (br m, 114), 4.20 (br m, 1H), 5.28 (br m, 1H), 9.40 (br s, 1H): $^{13}$C NMR (CDCl$_3$, 100 MHz) δ 11.8, 18.0, 26.5, 27.4, 30.1, 34.6, 55.0, 62.0, 68.4, 84.2, 156.7, 175.8.

Example 7

Preparation of 6-Methoxy-quinoxaline-2,3-diol (Compound 10)

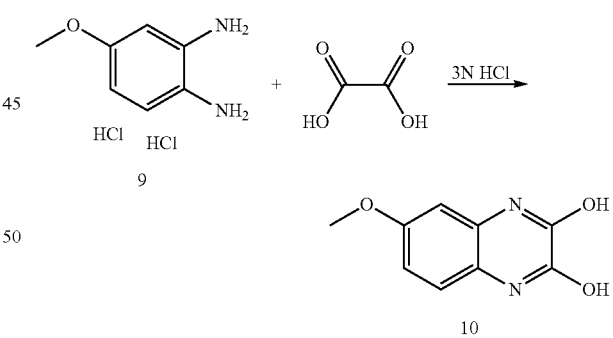

In a 50 L flask equipped with a mechanical stirrer, thermocouple and condenser was added 4-methoxy-1,2-phenylenediamine dihydrochloride salt (Compound 9) (2.65 kg @ 98 wt %, 12.30 mol), oxalic acid (1.582 kg @ 98 wt. %, 17.22 mol) and 3 N HCl$_{(aq)}$ (17.8 L) under nitrogen. The grey heterogeneous slurry was heated to 90° C. with steam for 7.25 hours. The reaction was monitored by HPLC. The resulting grey slurry was then cooled to an internal temperature of 20° C. overnight. The slurry was filtered, water (1.0-1.5 L/Kg) was used to help with the transfer. The light grey solids were washed with 2 cake volumes water (5.0-5.5 L/Kg). The solids were dried under vacuum/N$_2$ sweep for 24 hours, at which time the solids were still very wet. The product was then slurry washed with methanol, and dried over 48 hours at 40-45° C. in a vacuum oven to give Compound 10 as an off-white product of 99.95% purity by HPLC assay. There was no methanol by NMR and the KF=0.05 wt. % water.

HPLC Conditions:

Zorbax Eclipse Plus C18 50×4.6 mm, 1.8 um, 1.5 mL/min, 210 nm, 25° C., Eluents: Water 0.1% $H_3PO_4$ (A), Acetonitrile (B). 90% A 0 min, 5% A 5 min, 5% A 6 min

| | |
|---|---|
| Compound 9 (diamine HCl salt) | 0.394 min |
| Compound 10 | 1.55 min (sometimes two peaks) |

Example 8

Preparation of 2,3-Dichloro-6-methoxyquinoxaline (Compound 11)

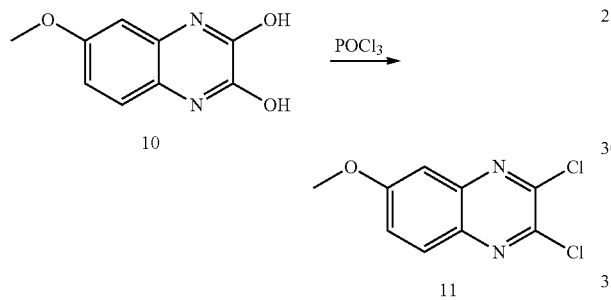

In a 22 L round bottomed flask equipped with a mechanical stirrer, thermocouple and condenser was added to 2,3-dichloro-6-methoxyquinoxalone Compound 10 (3.8 kg). Charged slowly at room temperature was $POCl_3$ (5.92 L @ 99%). The grey slurry was heated to 98° C. for 20 hours. After 2-3 hours the slurry turned from grey to green, then to yellow and finally turned homogeneous red. As the slurry became homogenous in $POCl_3$, significant amounts of HCl off-gassing were produced. The dark red, homogenous solution was allowed to cool slowly to below 80° C. At this point, 19 L of acetonitrile (5.0 L/Kg) was charged which produced a dark brown slurry. The reaction was cooled to 10-15° C. in an ice bath and reverse quenched into 45.6 L of cold water (12.0 L/Kg) in a 100 L cylindrical vessel. This exothermic quench was kept below 27° C. MeCN (~4 L) was used to aide in slurry transfer. The brown slurry was filtered and 5 L of water was used to wash the flask. The solids were washed with 1 cake volume of water (~5 L). The pH of the filtrate was acidic. The solids were next displacement washed with 2 cake volumes of 5% sodium bicarbonate (~20.00 L). The pH was between 8-9. A slurry wash was performed with 2 cake volumes of water (20 L total). The pH did not change. The solids were dried for 72 hours under reduced pressure and nitrogen flow to give tan product Compound 11 of 99.5% purity by HPLC assay with KF=0.5 wt. % water.

HPLC Conditions:

Zorbax Eclipse Plus C18 50×4.6 mm, 1.8 um, 1.5 mL/min, 210 nm, 25° C.; Eluents: Water 0.1% $H_3PO_4$ (A), Acetonitrile (B). 90% A 0 min, 5% A 5 min, 5% A 6 min.

| | |
|---|---|
| Compound 10 | 1.55 min (sometimes two peaks) |
| Compound 11 | 4.55 min |

An analytical sample was obtained by silica gel chromatography and as a colorless foam: $^1$H NMR (CDCl$_3$, 400 MHz) δ 0.50 (q, 1H, J=6.3 Hz), 1.04 (br s, 11H), 1.20 (br s, 3H), 1.45 (br s, 13H), 1.72 (m, 2H), 2.40 (m, 1H), 2.63 (m, 1H), 2.93 9 m, 2H), 3.68-3.94 (m, 9H), 4.15 (br m, 1H), 4.46 and 4.60 (t, due to rotamers, 1H, J=7.8 Hz), 5.27 (br m, 1H), 5.78 (br m, 1H), 7.18 (m, 1H), 7.20 (m, 1H), 7.85 (m, 1H); $^{13}$C NMR (CDCl$_3$, 100 MHz) δ 11.9, 18.5, 26.6, 27.0, 28.1, 28.3, 28.4, 29.1, 30.9, 32.9, 34.1, 35.7, 36.6, 49.4, 52.1, 52.2, 52.4, 55.1, 55.7, 57.7, 58.2, 62.3, 73.5, 74.1, 80.7, 106.0, 118.8, 128.5, 133.7, 141.1, 148.2, 153.9, 154.5, 155.3, 157.1, 160.4, 173.2, 173.3, 174.4.

Example 9

Preparation of (2S,4R)-4-(3-chloro-7-methoxyquinoxalin-2-yloxy)-2-(methoxycarbonyl)pyrrolidinium methanesulfonate (14)

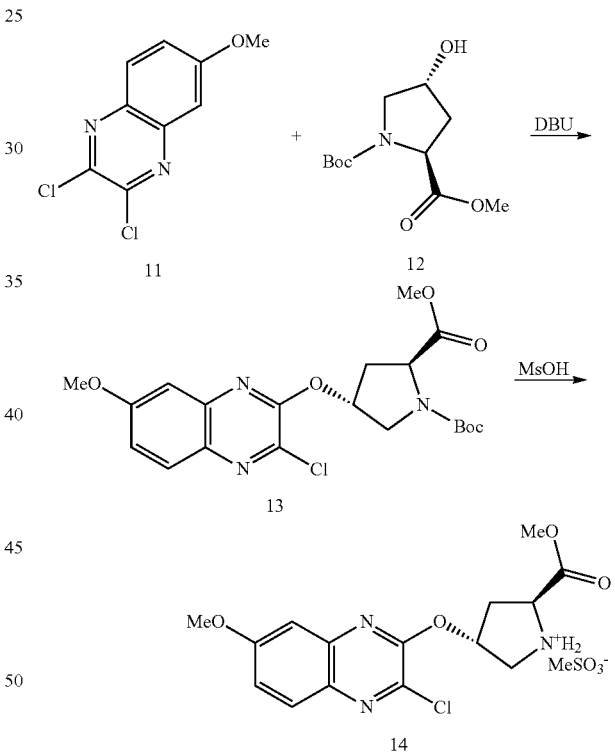

To a slurry of 2,3-dichloroquinoxaline 11 (100 g, 0.437 mol) and N-Boc-4-trans-hydroxy-L-proline methyl ester (12, 118 g, 0.48 mol) in DMAc (500 ml, KF<150) at ambient temperature was added DBU (86 g, 0.568 mol). The slurry was agitated at 40-45° C. for ~35 hours. The batch was then cooled to 15° C. Ethyl acetate (1.2 L) followed by citric acid (10%, 504 mL, 162 mmol) was added while the internal temperature was maintained <25° C. The organic phase was washed with a solution of 10% citric acid (200 mL) and water (200 mL) followed by water (400 mL×2). The organic phase was azeotropically dried and solvent switched to MeCN at a final volume of ~880 mL. MeSO$_3$H (36 mL, 0.555 mol) was added and the reaction mixture was aged at 40° C. for ~16 hours. To the reaction slurry was added MTBE (1.05 L) dropwise over 2 hours at 35° C. Then, the batch was further cooled to 0-5° C. and aged for 2-3 hours before filtration. The wet cake was displacement washed with 30% MeCN in MTBE (600 mL×2), and vacuum oven dried at 40° C. to give the product 14.

$^1$H NMR (400 MHz, d$_6$-DMSO) δ 9.74 (s, br, 2H), 7.86 (d, J=9.2 Hz, 1H), 7.34 (dd, J=9.2, 2.8 Hz, 1H), 7.26 (d, J=2.8 Hz, 1H), 5.77 (m 1H), 4.69 (dd, J=10.6, 7.6 Hz, 1H), 3.92 (s, 3H), 3.89 (dd, J=13.2, 5.2 Hz, 1H), 3.81 (s, 3H), 3.63 (m, 1H), 2.71 (m, 1H), 2.60 (m, 1H), 2.35 (s, 3H).

$^{13}$C NMR (100 MHz, d$_6$-DMSO) δ 168.3, 161.0, 151.8, 140.4, 135.4, 133.3, 128.6, 119.8, 106.0, 75.6, 58.0, 56.0, 53.2, 50.5, 39.6, 33.9.

HPLC conditions: Hypersil Gold PFP column, 150×4.6 mm, 3.0 um; Column temperature of 40° C.; Flow rate of 1.8 mL/min; and Wavelength of 215 nm.

| Gradient: | | |
| --- | --- | --- |
| min | CH$_3$CN | 0.1% H$_3$PO$_4$ |
| 0 | 25 | 75 |
| 12 | 70 | 30 |
| 12.1 | 25 | 75 |
| 14 | 25 | 75 |

| Retention times: | min. |
| --- | --- |
| Dichloroquinoxaline 11 | 7.8 |
| Proline quinoxaline 13 | 9.8 |
| De-Boc quinoxaline 14 | 3.6 |

Example 10

Preparation of (S)-2-(((1R,2R)-2-(5-(6-methoxy-3-((3R,5S)-5-(methoxycarbonyl)pyrrolidin-3-yloxy) quinoxalin-2-yl)pent-4-ynyl)cyclopropoxy)carbonylamino)-3,3-dimethylbutanoic acid (16) and alkyne macrocyclic ester (17)

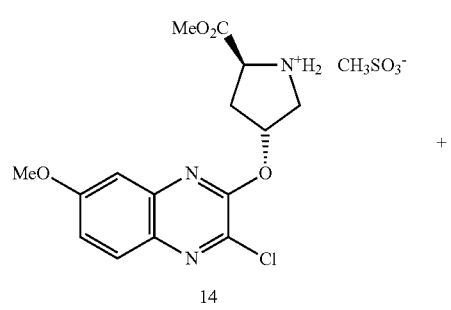

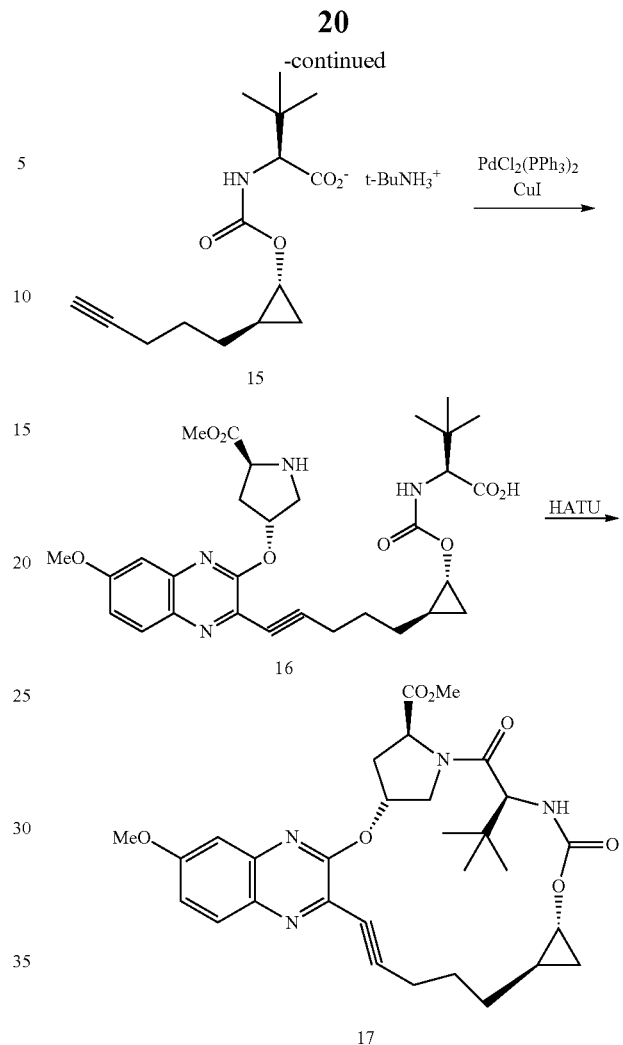

To a three-neck flask were added copper(I) iodide (0.219 g, 1.152 mmol), chloroquinoxaline MsOH salt 14 (50 g, 115 mmol), alkyne acid TBA salt 15 (49.3 g, 121 mmol), and bis(triphenylphosphine)palladium(II) dichloride (0.404 g, 0.573 mmol). The flask was vacuumed degassed with N$_2$. MeOH (500 ml) was added and the reaction mixture was vacuum degassed again with N$_2$. Triethylamine (32.1 ml, 230 mmol) was added. The reaction solution was aged at 35° C. for 3-5 hours. The batch was then concentrated to a volume of =100 mL in vacuum. THF (250 mL) and EtOAc (250 mL) were added. The reaction mixture was cooled to below 5° C. HCl solution (1 N, ~180 mL) was added slowly at below 5° C. until the reaction solution was pH adjusted to ~2. NaCl aq. solution (10%, 350 mL) was added. The separated aqueous phase was back-extracted with a solution of THF (250 mL) and EtOAc (250 mL). The combined organic phase was washed with 10% NaCl aq. solution (500 mL). The organic phase was azeotropically concentrated in vacuum with THF at below 20° C. until the KF of the solution was less than 500 ppm. Then, the reaction solvent was switched to DMAc (650 mL) in vacuum at below 20° C.

A solution of HATU (55.1 g, 145 mmol) in DMAc (650 mL) at ambient temperature was vacuumed degassed with N$_2$. The solution was then cooled to 0° C. and DIPEA (58.5 mL, 335 mmol) was added dropwise at below 0-5° C. Then, the above solution of alkyne quinoxaline acid 16 (65 g assay, 112 mmol) in DMAc was added dropwise over 10 hours, while maintaining the internal temperature at 0° C. After addition, the batch was agitated at 0° C. for additional 2 hours. EtOAc (750 mL) was added at below 5° C. A solution of 10% NaCl aq. solution (400 mL), water (125 mL) and 1 N HCl solution (100 mL) was slowly added while maintaining the batch temperature at below 5° C. The solution was then adjusted to pH=2 with 1 N HCl (~25 mL). The separated aqueous phase was back-extracted with EtOAc (500 mL). The combined organic phase was washed with 10% NaCl aq. solution (500 mL). After 10% NaCl aq. solution (500 mL) was added to the combined organic phase, the mixed solution was cooled to 0-5° C. 1 N NaOH aq. solution (~25 mL) was added to adjust the pH=~7. The separated organic phase was filtered through Celite and solvent switched to IPA at a final volume of 300 mL. Acetic acid (5.0 mL) was added, and the batch was then heated up to reflux for 30 min. The slurry was cooled to 60° C. and water (250 mL) was added dropwise over 1 hour. After addition, the batch was aged for additional 30 min before slowly cooling to ambient temperature in about 2 hours. After aging at least 1 hour, the batch was filtered. The wet cake was displacement washed with 50% aq IPA (100 mL). Suction dry at ambient temperature afforded 56 g of macrocyclic alkyne ester 17.

$^1$H NMR (400 MHz, CDCl$_3$) δ 7.80 (d, J=9.2 Hz, 1H), 7.17 (dd, J=9.2, 2.8 Hz, 1H), 7.04 (d, J=2.8 Hz, 1H), 5.82 (t, J=4.2 Hz, 1H), 5.26 (d, J=9.9 Hz, 1H), 4.62 (dd, J=10.3, 7.3 Hz, 1H), 4.51 (d, J=11.6 Hz, 1H), 4.40 (d, J=9.9 Hz, 1H), 4.03 (dd, J=11.6, 4.4 Hz, 1H), 3.91 (s, 3H), 3.87 (m, 1H), 3.73 (s, 3H), 2.85 (dt, J=12.1, 4.2 Hz, 1H), 2.76 (d, J=14.4, 7.3 Hz, 1H), 2.49 (dt, J=12.2, 5.4 Hz, 1H), 2.30 (ddd, J=14.6, 10.1, 4.2 Hz, 1H), 1.99 (m, 1H), 1.82 (m, 1H), 1.74 (m, 1H), 1.08 (s, 9H), 0.92 (m, 2H), 0.76 (m, 1H), 0.47 (m, 1H).

$^{13}$C NMR (100 MHz, CDCl$_3$) δ 172.3, 171.3, 161.2, 157.4, 156.3, 140.4, 134.3, 130.2, 129.5, 119.5, 105.7, 98.9, 75.5, 75.2, 59.4, 58.1, 55.7, 55.6, 54.1, 52.3, 35.3, 35.0, 29.9, 28.0, 26.3, 18.7, 18.3, 10.3.

IPC HPLC conditions: Ascentis Express C18 column, 100×4.6 mm, 2.7 micron; Column temperature of 40° C.; Flow rate of 1.8 mL/min; and Wavelength of 215 nm.

| Gradient: | | |
|---|---|---|
| min | CH$_3$CN | 0.1% H$_3$PO$_4$ |
| 0 | 10 | 90 |
| 6 | 95 | 5 |
| 9 | 95 | 5 |
| 9.1 | 10 | 90 |

| Retention times: | min. |
|---|---|
| De-Boc quinoxaline 14 | 2.3 |
| Alkyne quinoxaline acid 16 | 3.3 |
| Alkyne macrocyclic ester 17 | 5.7 |

Example 11

Preparation of Macrocyclic Ester 18

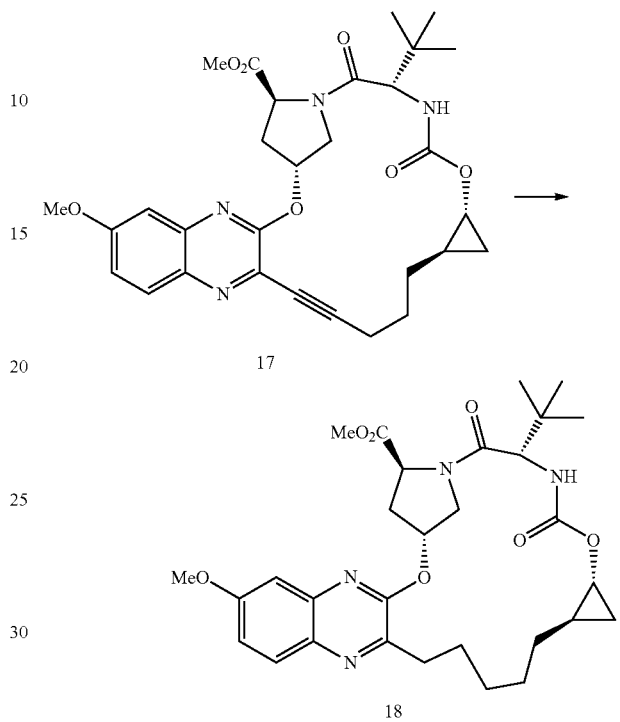

A mixture of alkyne macrocyclic ester 17 (10.0 g, 17.71 mmol) and 5% Pd/C 50% wet (3.5 g, 0.822 mmol) in THF (100 mL) was hydrogenated at ambient temperature under 40 psig of hydrogen for at least 10 hours. Upon reaction completion, the batch was filtered through Celite and the filtered catalyst was washed with THF (100 mL). The combined filtrate was solvent switched to IPA in vacuum at a final volume of ~50 mL. The slurry was heated up to reflux for about 1 hour. The batch was then cooled to 50° C. and water (30 mL) was added dropwise over 1 hour. The batch was slowly cooled to below 0° C. over 2 hour and stirred at 0° C. for additional 1 hour before filtration. The wet cake was washed with a cold solution (0-5° C.) of 57% IPA in water (17.5 mL). Suction dry at ambient temperature gave 8.5 g of the desired macrocyclic ester 18.

$^1$H NMR (400 MHz, CDCl$_3$) δ 7.83 (d, J=9.2 Hz, 1H), 7.18 (dd, J=9.2, 2.8 Hz, 1H), 7.1 (d, J=2.8 Hz, 1H), 5.98 (t, J=4.0 Hz, 1H), 5.24 (d, J=9.9 Hz, 1H), 4.60 (dd, J=10.7, 7.3 Hz, 1H), 4.46 (d, J=11.9 Hz, 1H), 4.40 (d, J=10.0 Hz, 1H), 4.01 (dd, J=11.6, 4.0 Hz, 1H), 3.93 (s, 3 μl), 3.80 (m, 1H), 3.75 (s, 3H), 2.90 (ddd, J=13.7, 11.5, 4.8 Hz, 1H), 2.79 (ddd, J=13.7, 12.1, 4.8 Hz, 1H), 2.69 (dd, J=14.2, 6.5 Hz, 1H), 2.28 (ddd, J=14.5, 10.7, 4.3 Hz, 1H), 1.76 (m, 2H), 1.66 (m, 2H), 1.52 (m, 3H), 1.09 (s, 9H), 0.99 (m, 1H), 0.92 (m, 1H), 0.67 (m, 1H), 0.46 (m, 1H).

$^{13}$C NMR (100 MHz, CDCl$_3$) δ 172.4, 171.5, 160.4, 157.5, 155.1, 148.7, 140.1, 134.6, 129.4, 118.7, 106.1, 74.4, 59.4, 58.2, 55.8, 55.5, 54.4, 52.5, 35.7, 35.2, 34.0, 30.9, 29.5, 28.6, 28.3, 26.5, 18.9, 11.2.

IPC HPLC conditions: Ascentis Express C18 Column, 100×4.6 mm, 2.7 micron; Column temperature or 40° C.; Flow rate or 1.8 mL/min; and Wavelength of 215 nm.

| Gradient: | | |
|---|---|---|
| min | CH₃CN | 0.1% H₃PO₄ |
| 0 | 10 | 90 |
| 6 | 95 | 5 |
| 9 | 95 | 5 |
| 9.1 | 10 | 90 |

| Retention times: | min. |
|---|---|
| Alkyne macrocyclicester 17 | 5.7 |
| cis-Alkene macrocyclic_ester (reaction intermediate) | 6.0 |
| trans-Alkene macrocyclic_ester (reaction intermediate) | 6.1 |
| Compound 18 | 6.2 |

Example 12

Preparation of Macrocyclic Acid (19)

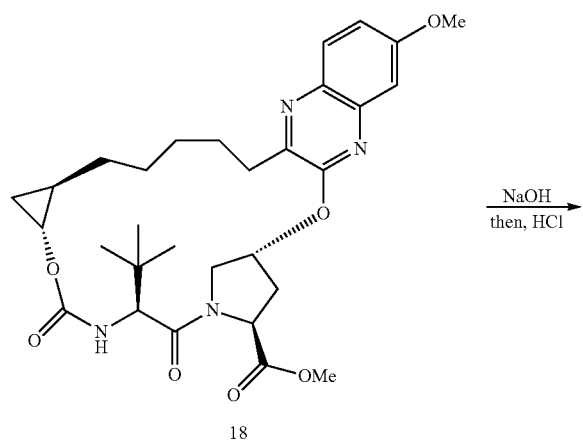

To a slurry of macrocyclic ester 18 (90 g, 158.3 mmol) in MeOH (720 mL) at ambient temperature was added 2 M NaOH (237.4 mL, 475 mmol) dropwise. The reaction mixture was aged at 50° C. for 2-3 hours. The reaction solution was cooled to 35-40° C. and 5 N HCl in 50% aq MeOH (70 mL) was added dropwise. The batch was seeded with free acid hemihydrate 19 (~100 mg) and aged for 30 min to 1 hour at 40° C. Additional 5 N HCl in 50% aq MeOH (30 mL) was added dropwise over 2-4 hours at 40° C. The slurry was aged additional 1 hour before cooling to ambient temperature. The slurry was aged for additional 1 hour before filtration. The wet cake was washed with 65% MeOH in water (3×270 mL, displacement wash, slurry wash and displacement wash). Suction dry at ambient temperature or vacuum oven dry with dry N₂ sweep at 60-80° C. gave 85.6 g of macrocyclic acid hemihydrate 19 as an off-white solid.

¹H NMR (400 MHz, CDCl₃) δ 7.85 (d, J=9.0 Hz, 1H), 7.19 (dd, J=9.0, 2.8 Hz, 1H), 7.13 (d, J=2.8 Hz, 1H), 5.99 (t, J=3.9 Hz, 1H), 5.45 (d, J=9.9 Hz, 1H), 4.80 (s, br, 2H, COOH, hemihydrate H₂O), 4.64 (dd, J=10.4, 7.4 Hz, 1H), 4.49 (d, J=11.6 Hz, 1H), 4.44 (d, J=10.0 Hz, 1H), 3.99 (dd, J=11.7, 4.0 Hz, 1H), 3.94 (s, 3H), 3.81 (m, 1H), 2.90 (ddd, J=13.8, 11.8, 4.8, 1H), 2.80 (ddd, J=13.8, 11.8, 4.8 Hz, 1H), 2.71 (dd, J=14.3, 7.3, 1H), 2.42 (ddd, J=14.4, 10.6, 4.2 Hz, 1H), 1.76 (m, 2H), 1.66 (m, 2H), 1.52 (m, 3H), 1.07 (s, 9H), 0.96 (m, 2H), 0.67 (m, 1H), 0.47 (m, 1H).

¹³C NMR (100 MHz, CDCl₃) δ 174.5, 172.1, 160.5, 157.6, 155.1, 148.6, 141.0, 134.3, 129.1, 118.9, 106.1, 74.3, 59.6, 58.3, 55.6, 54.6, 35.6, 35.3, 33.7, 30.8, 29.4, 28.6, 28.3, 26.5, 18.9, 11.2.

IPC HPLC conditions: Hypersil Gold PFP Column, 150× 4.6 mm, 3.0 μm, Column temperature of 40° C.; Flow rate of 1.8 mL/min; and Wavelength of 215 nm

| | min | CH₃CN | 0.1% H₃PO₄ |
|---|---|---|---|
| Gradient: | 0 | 25 | 75 |
| | 12 | 80 | 20 |
| | 12.1 | 25 | 75 |
| | 14 | 25 | 75 |

| Retention times: | min. |
|---|---|
| Compound 18 | 6.78 |
| Compound 19 | 5.41 |

Example 13

Preparation of Compound A

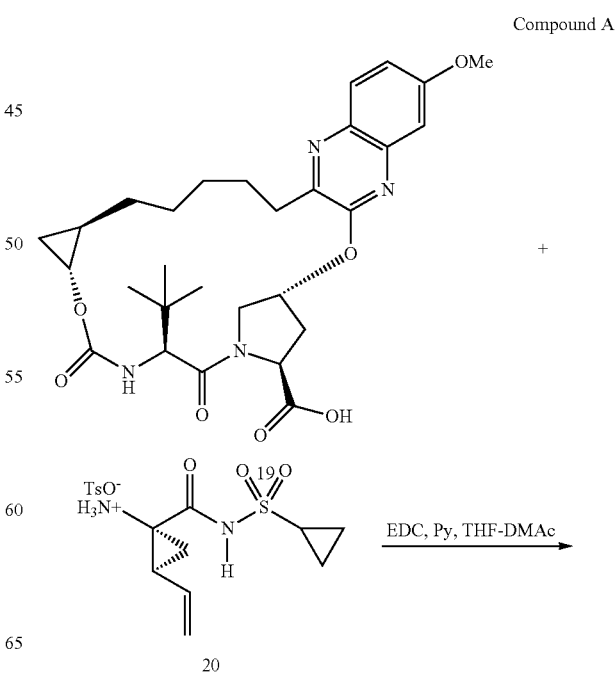

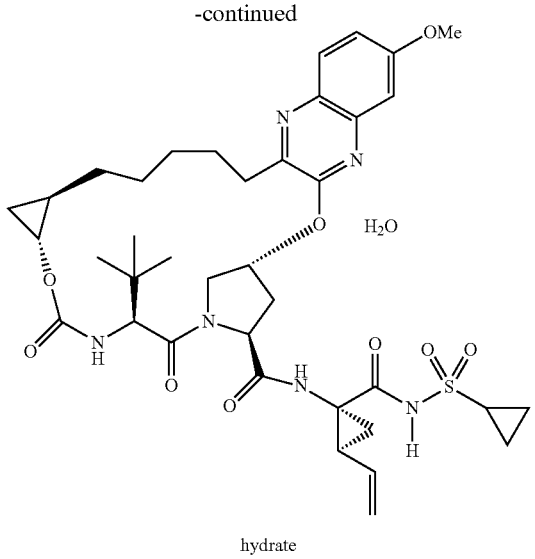

hydrate

Macrocyclic acid hemihydrate 19 (10.16 g, 18.03 mmol) was dissolved in THF (50-90 mL). The solution was azeotropically dried at a final volume of 100 mL. Sulfonamide pTSA salt 20 (7.98 g, 1.983 mmol) followed by DMAc (15 mL) was added at ambient temperature. The batch was cooled to 0-10° C. and pyridine (10 mL) was added dropwise. Then, EDC HCl (4.49 g, 23.44 mmol) was added in portions or one portion at 0-10° C. The reaction mixture was aged at 0-10° C. for 1 hour, then warmed to 15-20° C. for 2-4 hours. MeOAc (100 mL) followed by 15 wt % citric acid in 5% NaCl in water (50 mL) was added, while the internal temperature was maintained to <25° C. with external cooling. The separated organic phase was washed with 15 wt % citric acid in 5% NaCl in water (50 mL) followed by 5% NaCl (50 mL). The organic phase was solvent switched to acetone at a final volume of ~80 mL. Water (10 mL) was added dropwise at 35-40° C. The batch was seeded with Compound A monohydrate form III (~10 mg) and aged for 0.5-1 hour at 35-40° C. Additional water (22 mL) was added dropwise over 2-4 hours at 35-40° C. The slurry was aged at 20° C. for 2-4 hours before filtration. The wet cake was displacement washed with 60% acetone in water (40 mL×2). Suction dry at ambient temperature gave Compound A monohydrate form III as a white solid.

$^1$H NMR (400 MHz, CDCl$_3$) δ 9.95 (s, br, 1H), 7.81 (d, J=9.1 Hz, 1H), 7.18 (dd, J=9.1, 2.7 Hz, 1H), 7.16 (s, br, 1H), 7.13 (d, J=2.7 Hz, 1H), 5.96 (t, J=3.8 Hz, 1H), 5.72 (m, 1H), 5.68 (d, J=10.1 Hz, 1H), 5.19 (d, J=17.1 Hz, 1H), 5.07 (d, J=10.1 Hz, 1H), 4.52 (d, J=11.4 Hz, 1H), 4.45 (d, J=9.8 Hz, 1H), 4.36 (d, J=10.5, 6.9 Hz, 1H), 4.05 (dd, J=11.5, 3.9 Hz, 1H), 3.93 (s, 3H), 3.78 (m, 1H), 2.90 (m, 1H), 2.82 (tt, J=8.0, 4.8 Hz, 1H), 2.74 (dt, J=13.2, 4.8 Hz, 1H), 2.59 (dd, J=14.0, 6.7 Hz, 1H), 2.40 (ddd, J=14.0, 10.6, 4.0 Hz, 1H), 2.10 (dd, J=17.7, 8.7 Hz, 1H), 1.98 (2H, mono hydrate H$_2$O), 1.88 (dd, J 8.2, 5.9 Hz, 1H0, 1.74 (m, 3H), 1.61 (m, 1H), 1.50 (m, 3H), 1.42 (dd, J=9.6, 5.8 Hz, 1H), 1.22 (m, 2H), 1.07 (s, 9H), 0.95 (m, 4H), 0.69 (m, 1H), 0.47 (m, 1H).

$^{13}$C NMR (100 MHz, CDCl$_3$) δ 173.5, 172.1, 169.1, 160.4, 157.7, 154.9, 148.4, 141.0, 134.3, 132.7, 129.1, 118.8, 118.7, 106.5, 74.4, 59.6, 59.4, 55.8, 55.5, 54.9, 41.8, 35.4, 35.3, 35.2, 34.3, 31.2, 30.7, 29.5, 28.6, 28.2, 26.6, 22.6, 18.7, 11.2, 6.31, 6.17.

HPLC conditions: Ascentis Express Column, 10 cm×4.6 mm×2.7 μm; Column temperature of 40° C.; Flow rate of 1.8 mL/min; and Wavelength of 215 nm

|  | min | CH$_3$CN | 0.1% H$_3$PO$_4$ |
|---|---|---|---|
| Gradient: | 0 | 20 | 80 |
|  | 5 | 55 | 45 |
|  | 15 | 55 | 45 |
|  | 25 | 95 | 5 |
|  | 27 | 95 | 5 |
|  | 27.1 | 20 | 80 |
|  | 32 | 20 | 80 |

| Retention times: | min. |
|---|---|
| Compound A | 14.50 |

Example 14

Alternative Procedure for Making Compound A

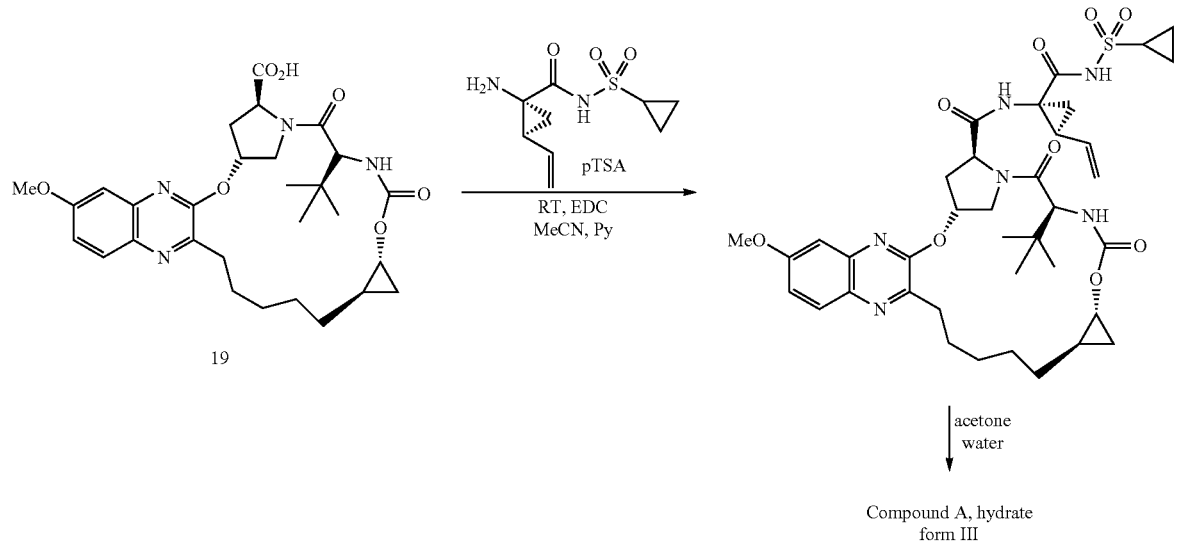

Compound A, hydrate form III

To a 50 L flask equipped with overhead stirring was added macrocyclic acid 19 (1.06 kg crude, 1.00 eq), amine-pTSA (862 g crude, 1.12 q) and MeCN 7.42 L at 19° C. The slurry was cooled in a water bath, pyridine (2.12 L, 13.8 eq) was added, aged 15 minutes, and then added EDC (586 g, 1.60 eq) in one portion, aged 1.5 hours while it turned into a clear homogeneous solution.

The solution cooled in a water bath, then quenched with 2 N HCl (1.7 L), seeded (9.2 g), aged 15 minutes, and the rest of the aqueous HCl was added over 2.5 hours. A yellow slurry was formed. The slurry was aged overnight at RT, filtered, washed with MeCN/water (1:1 v/v) 8 L, to obtain Compound A (Hydrate II).

Compound A was dissolved in acetone 4 L at RT, filtered and transferred to a 12 L RBF with overhead stirring, rinsed with extra acetone 1 L, heated to 50° C., water 0.9 L was added, seeded 10 g, aged 15 minutes, then added water 0.8 L over 2.5 hours, extra water 3.3 v over 2.5 hours was added, stopped heating, cooled to RT, aged at RT overnight, filtered, washed with water/acetone (1:1 v/v) 4 L, and dried in air under vacuum. Compound A Hydrate III, 670 g, was obtained as an off-white solid.

Example 15

Alternative Preparation of Macrocyclic Ester (18)

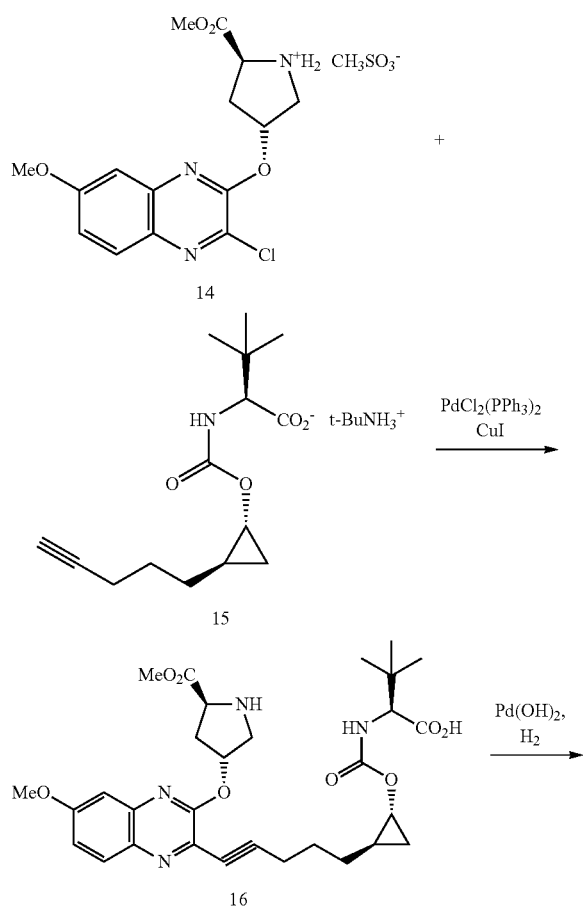

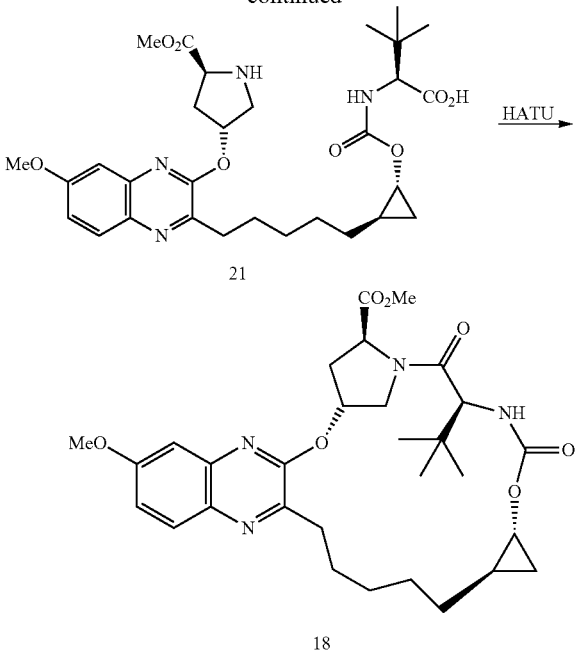

To a three-neck flask were added copper(I) iodide (0.020 g, 0.104 mmol), chloroquinoxaline MsOH salt 14 (4.5 g, 10.5 mmol), alkyne acid TBA salt 15 (4.4 g, 10.9 mmol), and bis(triphenylphosphine)palladium(II) dichloride (0.036 g, 0.052 mmol). The flask was vacuumed degassed with $N_2$. MeOH (45 ml) was added and the reaction mixture was vacuum degassed again with $N_2$. Triethylamine (2.89 ml, 20.7 mmol) was added. The reaction solution was aged at 35° C. for 3-5 hours. The batch was then concentrated to a volume of ~9 mL in vacuum. THF (23 mL) and EtOAc (23 mL) were added. The reaction mixture was cooled to below 5° C. HCl solution (1 N, ~16 mL) was added slowly at below 5° C. until the reaction solution was pH adjusted to ~2. NaCl aq. solution (10%, 32 mL) was added. The separated aqueous phase was back-extracted with a solution of THF (23 mL) and EtOAc (23 mL). The combined organic phase was washed with 10% NaCl aq. solution (45 mL). The solvent was switched to MeOH (75 mL) in vacuum at below 20° C.

To the reaction mixture was added DARCO KB-B (1.0 g), and the resulting suspension was stirred at 20° C. for 1 hour followed by filtration through Celite. The wet cake was washed with MeOH (25 mL). The combined filtrate was hydrogenated in the presence of Pearlman's catalyst (1.2 g, 20% $Pd(OH)_2$ on carbon, 50% wet) under 1 atmosphere of hydrogen at ambient temperature for at least 5 hours. Upon reaction completion, the suspension was filtered through Celite and the filtrate containing acid 21 was solvent switched to DMAc (65 mL).

A solution of HATU (5.05 g, 13.3 mmol) in DMAc (65 mL) at ambient temperature was vacuumed degassed with $N_2$. The solution was cooled to 0° C. and DIPEA (5.4 mL, 30.9 mmol) was added dropwise at 0-5° C. Then, the above solution of acid 21 (5.98 g assay, 10.2 mmol) in DMAc was added dropwise over 10 hours, while maintaining the internal temperature at 0° C. After addition, the batch was agitated at 0° C. for additional 2 hours to afford macrocyclic ester 18. The workup procedure and isolation of macrocyclic ester 18 were the same as described in Example 11.

Example 16

Compound A Hydrate II

Hydrate II was prepared by adding the Compound A free base to a solution to form an acetonitrile solvate and then drying at an elevated temperature.

Hydrate II were characterized by different methods including X-ray powder diffraction, a thermogravimetric analysis, and differential scanning calorimetry curve TG. The X-ray powder diffraction patterns were generated on a Philips Analytical X'Pert PRO X-ray Diffraction System with PW3040/60 console. A PW3373/00 ceramic Cu LEF X-ray tube K-Alpha radiation was used as the source.

DSC data were acquired using TA Instruments DSC 2910 or equivalent. Between 2 and 6 mg sample is weighed into a pan and covered. This pan is then crimped and placed at the sample position in the calorimeter cell. An empty pan is placed at the reference position. The calorimeter cell is closed and a flow of nitrogen is passed through the cell. The heating program is set to heat the sample at a heating rate of 10° C./min to a temperature of approximately 250° C. The heating program is started. When the run is completed, the data are analyzed using the DSC analysis program contained in the system software. The thermal events are integrated between baseline temperature points that are above and below the temperature range over which the thermal event is observed. The data reported are the onset temperature, peak temperature and enthalpy.

TG data were acquired using a Perkin Elmer model TGA 7. Experiments were performed under a flow of nitrogen and using a heating rate of 10° C./min to a maximum temperature of approximately 250° C. After automatically taring the balance, 5 to 20 mg of sample is added to the platinum pan, the furnace is raised, and the heating program started. Weight/temperature data are collected automatically by the instrument. Analysis of the results are carried out by selecting the Delta Y function within the instrument software and choosing the temperatures between which the weight loss is to be calculated. Weight losses are reported up to the onset of decomposition/evaporation.

FIG. 1 illustrates a characteristic X-ray diffraction pattern of the crystalline Hydrate II of Compound A. Hydrate II exhibited characteristic reflections corresponding to d-spacings of:

TABLE 1

| d-spacing [Å] | 2 theta | Relative Intensity |
|---|---|---|
| 7.594 | 11.654 | 100.00 |
| 5.348 | 16.577 | 94.28 |
| 7.898 | 11.204 | 70.04 |
| 5.874 | 15.082 | 69.31 |
| 5.521 | 16.054 | 59.34 |
| 3.865 | 23.014 | 47.39 |
| 4.257 | 20.867 | 47.22 |
| 11.071 | 7.986 | 40.56 |
| 3.725 | 23.890 | 39.30 |
| 3.561 | 25.006 | 37.79 |
| 5.273 | 16.813 | 35.33 |
| 4.985 | 17.795 | 33.23 |
| 4.493 | 19.759 | 30.78 |
| 3.954 | 22.487 | 24.45 |
| 10.639 | 8.311 | 24.44 |

Example 16

Hydrate III

Hydrate III was characterized by different methods including X-ray powder diffraction, a thermogravimetric analysis, differential scanning calorimetry curve TG, and solid-state carbon-13 nuclear magnetic resonance (NMR) spectra. The X-ray powder diffraction patterns were generated on a Philips Analytical X'Pert PRO X-ray Diffraction System with PW3040/60 console. A PW3373/00 ceramic Cu LEF X-ray tube K-Alpha radiation was used as the source.

DSC data were acquired using TA Instruments DSC 2910 or equivalent. Between 2 and 6 mg sample is weighed into a pan and covered. This pan is then crimped and placed at the sample position in the calorimeter cell. An empty pan is placed at the reference position. The calorimeter cell is closed and a flow of nitrogen is passed through the cell. The heating program is set to heat the sample at a heating rate of 10° C./min to a temperature of approximately 250° C. The heating program is started. When the run is completed, the data are analyzed using the DSC analysis program contained in the system software. The thermal events are integrated between baseline temperature points that are above and below the temperature range over which the thermal event is observed. The data reported are the onset temperature, peak temperature and enthalpy.

TG data were acquired using a Perkin Elmer model TGA 7. Experiments were performed under a flow of nitrogen and using a heating rate of 10° C./min to a maximum temperature of approximately 250° C. After automatically taring the balance, 5 to 20 mg of sample is added to the platinum pan, the furnace is raised, and the heating program started. Weight/temperature data are collected automatically by the instrument. Analysis of the results is carried out by selecting the Delta Y function within the instrument software and choosing the temperatures between which the weight loss is to be calculated. Weight losses are reported up to the onset of decomposition/evaporation.

The carbon-13 spectrum was recorded on a Bruker AV400 NMR spectrometer using a Bruker 4 mm H/F/X BB double resonance CPMAS probe. The spectrum were collected utilizing proton/carbon-13 variable-amplitude cross-polarization (VACP) at 80 kHz, with a contact time of 3 ms. Other experimental parameters used for data acquisition were a proton 90-degree pulse of 100 kHz, SPINAL64 decoupling at 100 kHz, a pulse delay of 2 s, and signal averaging for 26824 scans. The magic-angle spinning (MAS) rate was set to 13 kHz. A Lorentzian line broadening of 10 Hz was applied to the spectrum before Fourier Transformation. Chemical shifts are reported on the TMS scale using the carbonyl carbon of glycine (176.70 ppm) as a secondary reference.

FIG. 2 is a characteristic X-ray diffraction pattern of the crystalline Hydrate III. The Hydrate III exhibited characteristic reflections corresponding to d-spacings of:

TABLE 2

| d-spacing [Å] | 2 theta | Relative Intensity |
|---|---|---|
| 4.338 | 20.474 | 100.00 |
| 17.575 | 5.028 | 47.92 |
| 4.887 | 18.154 | 26.30 |
| 4.428 | 20.052 | 19.59 |
| 4.294 | 20.684 | 18.61 |
| 6.298 | 14.063 | 11.59 |
| 3.760 | 23.660 | 11.52 |
| 6.764 | 13.089 | 11.45 |

TABLE 2-continued

| d-spacing [Å] | 2 theta | Relative Intensity |
|---|---|---|
| 4.703 | 18.871 | 11.39 |
| 5.793 | 15.295 | 9.70 |
| 4.252 | 20.890 | 9.66 |
| 7.776 | 11.380 | 9.16 |
| 4.811 | 18.442 | 7.81 |
| 6.016 | 14.726 | 7.01 |
| 6.405 | 13.825 | 6.31 |

FIG. 3 illustrates a typical thermogravimetric analysis curve of the crystalline Hydrate III.

FIG. 4 illustrates a Differential scanning calorimetry curve of the crystalline Hydrate III.

FIG. 5 illustrates a solid state C-13 CPMAS NMR for Compound A Hydrate III. Characteristic peaks for Hydrate III are observed at 5.14, 6.31, 12.49, 18.35, 26.81, 28.03, 30.33, 31.27, 34.95, 35.99, 38.68, 42.01, 54.93, 56.39, 60.14, 74.20, 107.02, 120.11, 121.60, 129.73, 134.35, 135.95, 142.89, 148.47, 155.37, 157.32, 160.90, 168.32, 172.17, and 175.53 ppm.

Example 18

Additional Hydrates

Hydrates I, IV, V, and VI were characterized by X-ray powder diffraction and Carbon-13 NMR. The X-ray powder diffraction patterns were generated on a Philips Analytical X'Pert PRO X-ray Diffraction System with PW3040/60 console. A PW3373/00 ceramic Cu LEF X-ray tube K-Alpha radiation was used as the source. Carbon-13 spectrum was recorded on a Bruker AV400 NMR spectrometer using a Bruker 4 mm H/F/X BB double resonance CPMAS probe. The spectrum were collected utilizing proton/carbon-13 variable-amplitude cross-polarization (VACP) at 80 kHz with a proton 90-degree pulse of 100 kHz, SPINAL64 decoupling at 100 kHz. A Lorentzian line broadening of 30 Hz was applied to the spectrum before Fourier Transformation. Chemical shifts are reported on the TMS scale using the carbonyl carbon of glycine (176.70 ppm.) as a secondary reference. Other experimental parameters are outlined in each section below.

Hydrate I

Hydrate I was prepared by adding the free form to neat methanol, allowed to equilibrate for ~24 h at room temperature and air dried.

FIG. 8 is a characteristic X-ray diffraction pattern of the crystalline Hydrate Form I of Compound I of the present invention. The hydrate Form I exhibited characteristic reflections corresponding to d-spacings of:

TABLE 3

| 2 theta | d-spacing [Å] |
|---|---|
| 8.6 | 10.27 |
| 20.6 | 4.30 |
| 26.6 | 3.35 |
| 17.4 | 5.09 |
| 16.6 | 5.34 |
| 12.2, | 7.25 |
| 21.2 | 4.20 |
| 18.8 | 4.71 |
| 15.0 | 5.92 |
| 23.0 | 3.86 |
| 14.1 | 6.28 |
| 16.9 | 5.26 |

Hydrate I was characterized based on its solid-state carbon-13 nuclear magnetic resonance (NMR) spectrum. Other experimental parameters used for data acquisition were a pulse delay of 2 s, and signal averaging for 20480 scans. The magic-angle spinning (MAS) rate was set to 13 kHz and the temperature was set to 270 K. (FIG. 19.) Characteristic peaks for Hydrate I were observed at 4.22, 7.23, 11.45, 17.79, 24.04, 26.95, 28.29, 31.15, 32.47, 32.47, 33.46, 34.03, 35.74, 42.32, 53.50, 56.05, 56.96, 77.49, 108.95, 119.65, 122.55, 131.05, 133.13, 135.38, 142.28, 150.78, 156.03, 157.99, 161.36, 171.40, 173.42, 174.30 ppm.

Hydrate IV

Hydrate IV was prepared by adding the potassium salt to a solution of 1:1 Acetone:water with 1 equivalence of HCl and dried at RT.

FIG. 10 is a characteristic X-ray diffraction pattern of the crystalline Hydrate IV. The Hydrate IV exhibited characteristic reflections corresponding to d-spacings of:

TABLE 4

| 2 theta | d-spacing [Å] |
|---|---|
| 14.7 | 6.04 |
| 11.5 | 7.66 |
| 7.1 | 12.38 |
| 9.3 | 9.46 |
| 15.6 | 5.68 |
| 7.7 | 11.41 |
| 8.0 | 10.99 |

Hydrate IV was characterized based on its solid-state carbon-13 nuclear magnetic resonance (NMR) spectrum. Other experimental parameters used for data acquisition were a pulse delay of 2 s, and signal averaging for 1245 scans. The magic-angle spinning (MAS) rate was set to 13 kHz and the temperature was set to 275 K. (FIG. 11.) Characteristic peaks for Hydrate IV are observed at 3.90, 5.30, 6.99, 10.49, 13.13, 17.81, 24.73, 27.52, 28.14, 29.42, 31.02, 32.80, 36.08, 39.22, 42.45, 53.62, 55.93, 59.14, 60.76, 74.77, 109.22, 111.19, 11.38, 120.24, 122.50, 133.96, 139.74, 147.2, 148.90, 154.65, 158.25, 159.53, 160.12, 170.14, 171.05, 172.08, 173.47, and 174.46 ppm.

Hydrate V

Hydrate V was prepared by exposing Hydrate IV to relative humidity above 81%.

FIG. 12 is a characteristic X-ray diffraction pattern of the crystalline Hydrate V. The Hydrate V exhibited characteristic reflections corresponding to d-spacings of:

TABLE 5

| 2 theta | d-spacing [Å] |
|---|---|
| 9.1 | 9.7 |
| 18.3 | 4.8 |
| 19.8 | 4.5 |
| 15.2 | 5.8 |
| 23.2 | 3.8 |
| 10.9 | 8.1 |
| 17.6 | 5.0 |
| 23.9 | 3.7 |

Hydrate V was characterized based on its solid-state carbon-13 nuclear magnetic resonance (NMR) spectrum. (FIG. 13.) The spectrum was collected utilizing proton/carbon-13 variable-amplitude cross-polarization (VACP) at 80 kHz, with a contact time of 2 ms. Other experimental parameters used for data acquisition a pulse delay of 3 s, and signal averaging for 3425 scans. The magic-angle spinning (MAS)

rate was set to 13 kHz. Characteristic peaks for Hydrate V are observed at 7.86, 8.92, 13.10, 18.31, 23.72, 27.44, 28.47, 30.77, 35.79, 36.25, 37.15, 37.15, 42.95, 53.13, 55.67, 57.31, 60.47, 62.06, 75.09, 110.59, 112.24, 118.32, 132.18, 134.05, 135.83, 139.88, 148.30, 155.19, 157.97, 159.41, 170.31 and 175.20 ppm.

Hydrate VI

Hydrate VI was prepared by adding the free base to a 50/50 mixture of methanol/acetone and drying at room temperature.

FIG. 14 is a characteristic X-ray diffraction pattern of the crystalline Hydrate VI. The Hydrate VI exhibited characteristic reflections corresponding to d-spacings of:

TABLE 6

| d-spacing [Å] | 2 theta |
|---|---|
| 4.3 | 20.5 |
| 6.9 | 12.8 |
| 4.6 | 19.4 |
| 4.2 | 21.2 |
| 5.3 | 16.8 |
| 6.4 | 13.9 |
| 17.9 | 5.0 |
| 4.8 | 18.5 |
| 3.8 | 23.7 |
| 3.3 | 26.8 |

Hydrate VI was characterized based on its solid-state carbon-13 nuclear magnetic resonance (NMR) spectrum. (FIG. 15.) The spectrum was collected utilizing proton/carbon-13 variable-amplitude cross-polarization (VACP) at 80 kHz, with a contact time of 3 ms. Other experimental parameters used for data acquisition were a pulse delay of 2 s, and signal averaging for 3425 scans.

Characteristic peaks for Hydrate VI are observed at 4.87, 6.24, 11.70, 12.85, 18.36, 26.55, 28.31 m 31.51, 34.98, 38.47, 42.09, 54.27, 56.12, 60.10, 73.49, 73.97, 105.91, 108.04, 118.39, 119.75, 121.33, 129.96, 133.87, 136.13, 142.26, 142.97, 146.85, 148.36, 154.97, 157.32, 160.71, 168.23, 172.21 and 175.34 ppm.

Relative stability in water of Hydrates I, II, and III showed predominantly Hydrate II after 12 hours and predominantly Hydrate III after 5 days. Relative stability of Hydrate II, III and IV showed predominantly Hydrate III in acetone, water and mixtures thereof at 25° C. and 50° C.

The relative stability of the hydrate forms was determined by competitive slurry turnover experiments in Acetone:water at water activities ranging from 0.072 to 1 at room temperature. In all cases, the Hydrate form III was the resultant solids from these experiments indicating that this is the most stable of the hydrate forms in the solvents investigated.

Example 19

Compound A K$^+$ and Na$^+$ Salt Production

Compound A K$^+$ and Na$^+$ salts were produced as follows: Preparation of Compound K Na-Salt

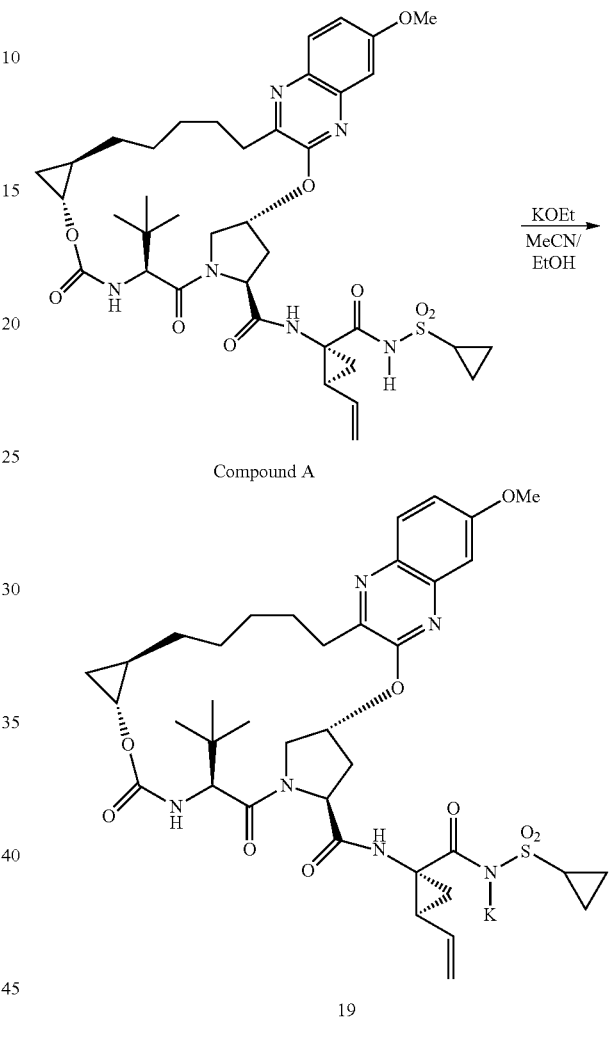

To a 50 L jacketed cylindrical vessel equipped with a mechanical stirrer, thermocouple and nitrogen inlet containing 30 L 2:1 MeCN:EtOH was added the 3.3 kg Compound A free acid. This was then transferred through an in-line filter to a 72 L RBF equipped with a mechanical stirrer, thermocouple and nitrogen inlet. To this solution was added over 1 hour the KOEt in EtOH. The solution was seeded with the form II after addition of 20% of the KOEt in EtOH. The resulting slurry was stirred for 3 hour at ambient temperature and then filtered.

| Materials | MW | Amount | Moles | Equiv |
|---|---|---|---|---|
| Compound A free acid | 766.90 | 3.4 kg | 4.18 | 1.00 |
| KOEt in EtOH 24 wt % | 84.16 | 1.97 L | 5.02 | 1.20 |
| MeCN | | 30 L | | |
| EtOH | | 10 L | | |

The suspension was then filtered, washed with 2×10 L of MeCN and dried under N$_2$/vacuum sweep to yield 3.40 kg of Compound A potassium salt (98.3 wt %, 98.1 LCAP, 99% yield).

HPLC Conditions:

Zorbax Eclipse Plus C18 50×4.6 mm, 1.8 μm, A=0.1% phosphoric acid, C=Acetonitrile: 10% to 95% C, 5 min; 95% C, 6 min; 10% C, 6.1 min; 2 min post, 1.5 mL/min, 230 nm, 25° C.

Compound A 5.41 min

Preparation of Compound A Na-Salt

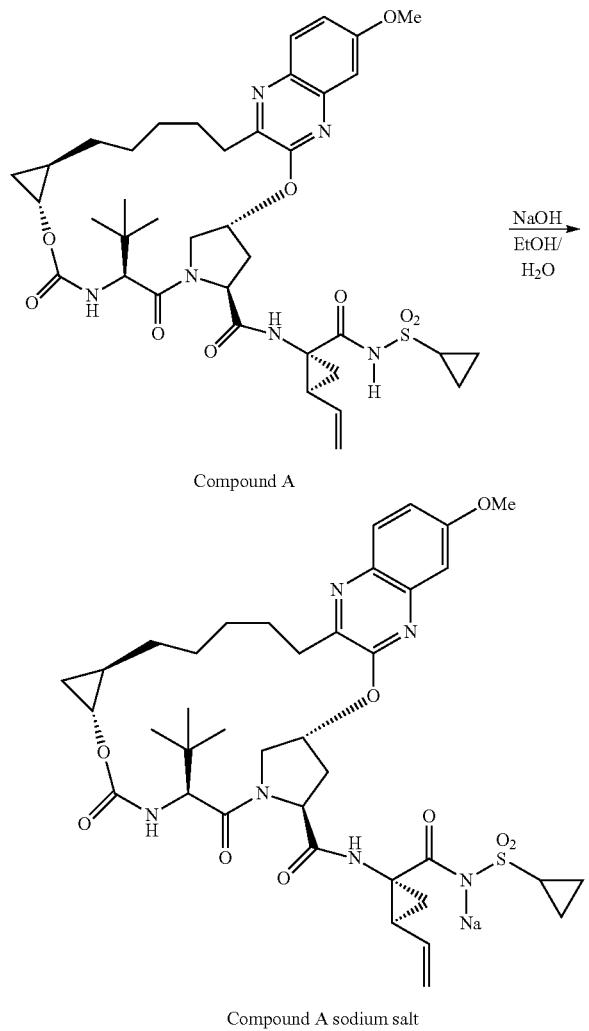

Compound A

Compound A sodium salt

| Materials | MW | Amount | mMol | Equiv |
|---|---|---|---|---|
| Compound A free acid | 766.90 | 2 g | 2.61 | 1.00 |
| NaOH (2M) | 40.00 | 1.30 mL | 2.61 | 1.00 |
| EtOH | | 40 mL | | |
| H$_2$O | | 0.2 mL | | |

In a 100 mL 2 necked round bottom flask under nitrogen, Compound A free acid was dissolved in 40 mL EtOH with 0.2 mL water added at 50° C. To this was added slowly over 30 min the 1.30 mL 2 M sodium hydroxide solution, held at 50° C. until a solid was formed and then allowed to cool slowly to room temperature and age for 3 hours. The slurry was then cooled in an ice bath and the suspension was then filtered, washed with 2×10 mL of MeCN and dried under N$_2$/vacuum sweep to yield 2.01 g of Compound A sodium salt (98.3 LCAP, 99% yield).

HPLC Conditions:

Zorbax Eclipse Plus C18 50×4.6 mm, 1.8 μm, A=0.1% phosphoric acid, C=Acetonitrile: 10% to 95% C, 5 min; 95% C, 6 min; 10% C, 6.1 min; 2 min post, 1.5 mL/min, 230 nm, 25° C.

| Compound A | 5.41 min |
|---|---|

Example 20

Compound A K$^+$ and Na$^+$ Salt Characterization

The X-ray powder diffraction patterns were generated on a Philips Analytical X'Pert PRO X-ray Diffraction System with PW3040/60 console. A PW3373/00 ceramic Cu LEF X-ray tube K-Alpha radiation was used as the source.

DSC data were acquired using TA Instruments DSC 2910 or equivalent. Between 2 and 6 mg sample is weighed into a pan and covered. This pan is then crimped and placed at the sample position in the calorimeter cell. An empty pan is placed at the reference position. The calorimeter cell is closed and a flow of nitrogen is passed through the cell. The heating program is set to heat the sample at a heating rate of 10° C./min to a temperature greater than 300° C. The heating program is started. When the run is completed, the data are analyzed using the DSC analysis program contained in the system software. The thermal events are integrated between baseline temperature points that are above and below the temperature range over which the thermal event is observed. The data reported are the onset temperature, peak temperature and enthalpy.

TG data were acquired using a Perkin Elmer model TGA 7. Experiments were performed under a flow of nitrogen and using a heating rate of 10° C./min to a maximum temperature greater than 300° C. After automatically taring the balance, 5 to 20 mg of sample is added to the platinum pan, the furnace is raised, and the heating program started. Weight/temperature data are collected automatically by the instrument. Analysis of the results are carried out by selecting the Delta Y function within the instrument software and choosing the temperatures between which the weight loss is to be calculated. Weight losses are reported up to the onset of decomposition/evaporation.

Compound A Na-salt

FIG. 6 illustrates a characteristic X-ray diffraction pattern of the crystalline Na-salt of Compound A. The Na-salt exhibited characteristic reflections corresponding to d-spacings of:

TABLE 7

| d-spacing [Å] | Pos. [°2Th.] | Rel. Int. [%] |
|---|---|---|
| 4.8 | 18.4 | 82.2 |
| 9.7 | 9.1 | 59.5 |
| 9.1 | 9.8 | 49.0 |
| 9.3 | 9.6 | 25.1 |
| 4.6 | 19.3 | 25.1 |
| 5.8 | 15.3 | 23.6 |
| 5.4 | 16.5 | 20.2 |
| 4.0 | 22.5 | 18.5 |
| 5.1 | 17.4 | 17.9 |
| 4.4 | 20.2 | 16.6 |

TABLE 7-continued

| d-spacing [Å] | Pos. [°2Th.] | Rel. Int. [%] |
|---|---|---|
| 10.6 | 8.4 | 16.4 |
| 4.2 | 21.3 | 16.0 |
| 3.3 | 26.9 | 15.0 |
| 18.3 | 4.8 | 14.8 |
| 3.4 | 26.2 | 14.7 |

Compound A K-salt

FIG. 11 illustrates a characteristic X-ray diffraction pattern of the crystalline K-salt of Compound A. The K-salt exhibited characteristic reflections corresponding to d-spacings of:

TABLE 8

| d-spacing [Å] | Pos. [°2Th.] | Rel. Int. [%] |
|---|---|---|
| 4.9 | 18.2 | 100.0 |
| 10.0 | 8.9 | 49.1 |
| 4.4 | 20.3 | 32.3 |
| 4.7 | 18.7 | 27.9 |
| 4.0 | 22.5 | 27.2 |
| 10.5 | 8.4 | 24.7 |
| 4.5 | 19.6 | 22.6 |
| 5.3 | 16.7 | 20.6 |
| 3.3 | 27.1 | 19.2 |
| 8.6 | 10.3 | 19.0 |
| 4.1 | 21.9 | 17.9 |
| 9.4 | 9.4 | 16.4 |
| 4.2 | 21.2 | 15.6 |
| 3.4 | 25.9 | 15.5 |
| 7.1 | 12.5 | 15.1 |

None of the references described throughout the present application are admitted to be prior art to the claimed invention.

What is claimed is:

1. Compound A having a form selected from the group consisting of:
   a) Hydrate III, wherein Hydrate III is characterized by (i) an X-ray powder diffraction pattern obtained using copper $K_\alpha$ radiation which comprises 2Θ values in degrees of about 20.5, 5.0, and 18.2; and/or (ii) a solid state carbon-13 CPMAS NMR comprising peaks at about 5.14, 6.31, 12.49, 18.35, 26.81, 28.03, 30.33, 31.27, 34.95, 35.99, 38.68, 42.01, 54.93, 56.39, 60.14, 74.20, 107.02, 120.11, 121.60, 129.73, 134.35, 135.95, 142.89, 148.47, 155.37, 157.32, 160.90, 168.32, 172.17, and 175.53 ppm;
   b) Hydrate II, wherein Hydrate II is characterized by an X-ray powder diffraction pattern obtained using copper $K_\alpha$ radiation which comprises 2Θ values in degrees of about 11.7, 16.6, and 11.2;
   c) a crystalline Na salt characterized by an X-ray powder diffraction pattern obtained using copper $K_\alpha$ radiation which comprises 2Θ values in degrees of about 18.4, 9.1, and 9.8;
   d) Hydrate I, wherein Hydrate I is characterized by (i) an X-ray powder diffraction pattern obtained using copper $K_\alpha$ radiation which comprises 2Θ values in degrees of about 8.6, 20.6, and 26.6; and/or (ii) a solid state carbon-13 CPMAS NMR comprising peaks at about 4.22, 7.23, 11.45, 17.79, 24.04, 26.95, 28.29, 31.15, 32.47, 32.47, 33.46, 34.03, 35.74, 42.32, 53.50, 56.05, 56.96, 77.49, 108.95, 119.65, 122.55, 131.05, 133.13, 135.38, 142.28, 150.78, 156.03, 157.99, 161.36, 171.40, 173.42, 174.30 ppm;
   e) Hydrate IV, wherein Hydrate IV is characterized by (i) an X-ray powder diffraction pattern obtained using copper $K_\alpha$ radiation which comprises 2Θ values in degrees of about 14.7, 11.5, and 7.1; and/or (ii) a solid state carbon-13 CPMAS NMR comprising peaks at about 3.90, 5.30, 6.99, 10.49, 13.13, 17.81, 24.73, 27.52, 28.14, 29.42, 31.02, 32.80, 36.08, 39.22, 42.45, 53.62, 55.93, 59.14, 60.76, 74.77, 109.22, 111.19, 11.38, 120.24, 122.50, 133.96, 139.74, 147.2, 148.90, 154.65, 158.25, 159.53, 160.12, 170.14, 171.05, 172.08, 173.47, and 174.46 ppm;
   f) Hydrate V, wherein Hydrate V is characterized by (i) an X-ray powder diffraction pattern obtained using copper $K_\alpha$ radiation which comprises 2Θ values in degrees of about 9.1, 18.3, and 19.8; and/or (ii) a solid state carbon-13 CPMAS NMR comprising peaks at about 7.86, 8.92, 13.10, 18.31, 23.72, 27.44, 28.47, 30.77, 35.79, 36.25, 37.15, 37.15, 42.95, 53.13, 55.67, 57.31, 60.47, 62.06, 75.09, 110.59, 112.24, 118.32, 132.18, 134.05, 135.83, 139.88, 148.30, 155.19, 157.97, 159.41, 170.31 and 175.20; and
   g) Hydrate VI, wherein Hydrate VI is characterized by (i) an X-ray powder diffraction pattern obtained using copper $K_\alpha$ radiation which comprises 2Θ values in degrees of about 20.5, 12.8, and 19.4; and/or (ii) a solid state carbon-13 CPMAS NMR comprising peaks at about 4.87, 6.24, 11.70, 12.85, 18.36, 26.55, 28.31 m 31.51, 34.98, 38.47, 42.09, 54.27, 56.12, 60.10, 73.49, 73.97, 105.91, 108.04, 118.39, 119.75, 121.33, 129.96, 133.87, 136.13, 142.26, 142.97, 146.85, 148.36, 154.97, 157.32, 160.71, 168.23, 172.21 and 175.34 ppm.

2. A pharmaceutical composition comprising a therapeutically effect amount of a compound of claim 1 and a pharmaceutically acceptable carrier.

3. A method of treating HCV in a patient comprising the step of administering to the patient a therapeutically effective amount of a compound of claim 1.

4. A method of treating HCV in a patient, said method comprising administering an effective amount of a compound of claim 1 to the patient.

5. The compound of claim 1 for use in the treatment of HCV.

6. A method of making a compound of claim 1, where said Compound A is Hydrate III, made by a process comprising crystallising Compound A using an acetone/water ratio of 80:20 v/v acetone to water to 0:100 v/v acetone to water and drying.

* * * * *